United States Patent
Scirica et al.

(10) Patent No.: US 10,779,827 B2
(45) Date of Patent: Sep. 22, 2020

(54) SURGICAL STAPLING DEVICE WITH DISSECTING TIP

(71) Applicant: Covidien LP, Mansfield, MA (US)

(72) Inventors: Paul Scirica, Huntington, CT (US); Todd Demmy, East Amherst, NY (US); Lee Ann Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 249 days.

(21) Appl. No.: 15/921,268

(22) Filed: Mar. 14, 2018

(65) Prior Publication Data

US 2018/0199942 A1    Jul. 19, 2018

Related U.S. Application Data

(63) Continuation of application No. 15/227,482, filed on Aug. 3, 2016, now Pat. No. 9,943,311, which is a continuation of application No. 11/665,108, filed as application No. PCT/US2004/013291 on Apr. 29, 2004, now Pat. No. 9,597,078, which is a continuation of application No. 10/764,103, filed on Jan. 23, 2004.

(60) Provisional application No. 60/466,378, filed on Apr. 29, 2003.

(51) Int. Cl.
*A61B 17/072*    (2006.01)

(52) U.S. Cl.
CPC .................. *A61B 17/07207* (2013.01); *A61B 2017/07214* (2013.01); *A61B 2017/07221* (2013.01); *A61B 2017/07257* (2013.01); *A61B 2017/07271* (2013.01)

(58) Field of Classification Search
CPC .... A61B 17/07207; A61B 2017/07271; A61B 2017/07257; A61B 2017/07221; A61B 2017/07214; A61B 2017/320044
USPC ............ 227/175.1–182.1; 606/139, 142, 143
See application file for complete search history.

(56) References Cited

U.S. PATENT DOCUMENTS

| | | | |
|---|---|---|---|
| 2,679,249 A | * | 5/1954 | Maximiliano ......... A61B 17/32 606/174 |
| 2,887,111 A | | 5/1959 | Diaz |
| 3,079,606 A | | 3/1963 | Bobrov et al. |
| 3,490,675 A | | 1/1970 | Green et al. |
| 3,604,561 A | * | 9/1971 | Mallina .............. A61B 17/0686 206/339 |
| 4,429,695 A | | 2/1984 | Green |
| 4,505,414 A | | 3/1985 | Filipi |
| 4,589,413 A | | 5/1986 | Malyshev et al. |
| 4,602,634 A | | 7/1986 | Barkley |
| 4,608,981 A | | 9/1986 | Rothfuss et al. |

(Continued)

FOREIGN PATENT DOCUMENTS

| | | |
|---|---|---|
| DE | 1213426 B | 3/1966 |
| DE | 2744824 A1 | 4/1978 |

(Continued)

*Primary Examiner* — Robert F Long
(74) *Attorney, Agent, or Firm* — Carter, DeLuca & Farrell LLP

(57) ABSTRACT

A dissecting tip is provided for use with a surgical stapler or instrument. In one embodiment, the dissecting tip is secured to the end effector of a surgical stapler, e.g., to the anvil assembly or cartridge assembly. The dissecting tip extends distally from the end effector and is configured to dissect or separate target tissue from certain tissue, e.g., adherent, connective, joined or other tissue.

20 Claims, 29 Drawing Sheets

(56) References Cited

U.S. PATENT DOCUMENTS

| | | | |
|---|---|---|---|
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,703,887 A | 11/1987 | Clanton et al. | |
| 4,728,020 A | 3/1988 | Green et al. | |
| 4,784,137 A | 11/1988 | Kulik et al. | |
| 4,815,465 A * | 3/1989 | Alvarado | A61B 17/128 606/139 |
| 4,863,088 A | 9/1989 | Redmond et al. | |
| 4,892,244 A | 1/1990 | Fox et al. | |
| 4,915,100 A * | 4/1990 | Green | A61B 17/072 227/176.1 |
| 4,991,764 A | 2/1991 | Mericle | |
| 5,040,715 A | 8/1991 | Green et al. | |
| 5,065,929 A | 11/1991 | Schulze et al. | |
| 5,074,454 A | 12/1991 | Peters | |
| 5,083,695 A | 1/1992 | Foslien et al. | |
| 5,100,418 A * | 3/1992 | Yoon | A61B 17/0487 606/139 |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,170,925 A | 12/1992 | Madden et al. | |
| 5,219,354 A | 6/1993 | Choudhury et al. | |
| RE34,519 E | 1/1994 | Fox et al. | |
| 5,307,976 A | 5/1994 | Olson et al. | |
| 5,312,023 A | 5/1994 | Green et al. | |
| 5,318,221 A | 6/1994 | Green et al. | |
| 5,326,013 A | 7/1994 | Green et al. | |
| 5,332,142 A | 7/1994 | Robinson et al. | |
| 5,337,937 A * | 8/1994 | Remiszewski | A61B 17/0686 227/182.1 |
| 5,364,003 A | 11/1994 | Williamson, IV | |
| 5,376,095 A | 12/1994 | Ortiz | |
| 5,381,943 A | 1/1995 | Allen et al. | |
| 5,383,880 A | 1/1995 | Hooven | |
| 5,389,098 A * | 2/1995 | Tsuruta | A61B 17/00234 606/41 |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,405,344 A * | 4/1995 | Williamson | A61B 17/1285 606/1 |
| 5,407,293 A | 4/1995 | Crainich | |
| 5,415,334 A | 5/1995 | Williamson et al. | |
| 5,415,335 A | 5/1995 | Knodell, Jr. | |
| 5,417,361 A | 5/1995 | Williamson, IV | |
| 5,431,323 A | 7/1995 | Smith et al. | |
| 5,433,721 A | 7/1995 | Hooven et al. | |
| 5,447,265 A | 9/1995 | Vidal et al. | |
| 5,452,837 A | 9/1995 | Williamson, IV et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,474,566 A | 12/1995 | Alesi et al. | |
| 5,476,206 A * | 12/1995 | Green | A61B 17/07207 227/176.1 |
| 5,484,451 A | 1/1996 | Akopov et al. | |
| 5,485,947 A | 1/1996 | Olson et al. | |
| 5,487,500 A | 1/1996 | Knodel et al. | |
| 5,489,058 A | 2/1996 | Plyley et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,937 A | 7/1996 | Boiarski et al. | |
| 5,551,622 A | 9/1996 | Yoon | |
| 5,553,765 A | 9/1996 | Knodel et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,573,543 A | 11/1996 | Akopov et al. | |
| 5,577,654 A | 11/1996 | Bishop | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,601,578 A * | 2/1997 | Murphy | A61B 17/0469 606/148 |
| 5,607,095 A | 3/1997 | Smith et al. | |
| 5,624,452 A | 4/1997 | Yates | |
| 5,626,587 A | 5/1997 | Bishop et al. | |
| 5,626,595 A * | 5/1997 | Sklar | A61B 17/320016 606/170 |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,665,100 A | 9/1997 | Yoon | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,680,982 A | 10/1997 | Schulze et al. | |
| 5,690,269 A | 11/1997 | Bolanos et al. | |
| 5,690,653 A | 11/1997 | Richardson et al. | |
| 5,692,668 A | 12/1997 | Schulze et al. | |
| 5,697,542 A | 12/1997 | Knodel et al. | |
| 5,704,534 A | 1/1998 | Huitema et al. | |
| 5,709,334 A | 1/1998 | Sorrentino et al. | |
| 5,711,472 A | 1/1998 | Bryan | |
| 5,713,505 A | 2/1998 | Huitema | |
| 5,716,366 A | 2/1998 | Yates | |
| 5,728,110 A | 3/1998 | Vidal et al. | |
| 5,728,112 A * | 3/1998 | Yoon | A61B 17/04 606/139 |
| 5,735,848 A | 4/1998 | Yates et al. | |
| 5,743,456 A | 4/1998 | Jones et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,762,256 A | 6/1998 | Mastri et al. | |
| 5,769,303 A | 6/1998 | Knodel et al. | |
| 5,772,099 A | 6/1998 | Gravener | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,811 A | 9/1998 | Yates et al. | |
| 5,810,855 A | 9/1998 | Rayburn et al. | |
| 5,816,471 A | 10/1998 | Plyley et al. | |
| 5,817,109 A | 10/1998 | McGarry et al. | |
| 5,820,009 A | 10/1998 | Melling et al. | |
| 5,823,066 A | 10/1998 | Huitema et al. | |

(56) References Cited

U.S. PATENT DOCUMENTS

| | | |
|---|---|---|
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,941,442 A | 8/1999 | Geiste et al. |
| 5,954,259 A | 9/1999 | Viola et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,197,017 B1 | 3/2001 | Brook et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,439,446 B1 | 8/2002 | Perry et al. |
| 6,443,973 B1 | 9/2002 | Whitman |
| 6,446,854 B1 | 9/2002 | Remiszewski et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,582,451 B1 * | 6/2003 | Marucci .......... A61B 17/29 606/207 |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,656,193 B2 | 12/2003 | Grant et al. |
| 6,698,643 B2 | 3/2004 | Whitman |
| 6,722,552 B2 | 4/2004 | Fenton, Jr. |
| 7,208,005 B2 * | 4/2007 | Frecker .......... A61B 17/29 606/167 |
| 7,867,243 B2 * | 1/2011 | Crainich .......... A61B 17/0682 606/142 |
| 9,943,311 B2 | 4/2018 | Scirica et al. |
| 2005/0119669 A1 * | 6/2005 | Demmy .......... A61B 17/07207 606/139 |
| 2008/0237297 A1 * | 10/2008 | Demmy .......... A61B 17/07207 227/176.1 |
| 2008/0269793 A1 * | 10/2008 | Scirica .......... A61B 17/07207 606/190 |
| 2017/0128070 A1 * | 5/2017 | Scirica .......... A61B 17/07207 |

FOREIGN PATENT DOCUMENTS

| | | |
|---|---|---|
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0065188 A2 | 11/1982 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0621006 A1 | 10/1994 |
| EP | 0621009 A1 | 10/1994 |
| EP | 0656188 A1 | 6/1995 |
| EP | 0666057 A2 | 8/1995 |
| EP | 0705571 A1 | 4/1996 |
| EP | 0760230 A1 | 3/1997 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| SU | 659146 A1 | 4/1979 |
| SU | 728848 A1 | 4/1980 |
| SU | 980703 A1 | 12/1982 |
| SU | 990220 A1 | 1/1983 |
| WO | 8302247 A1 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |

\* cited by examiner

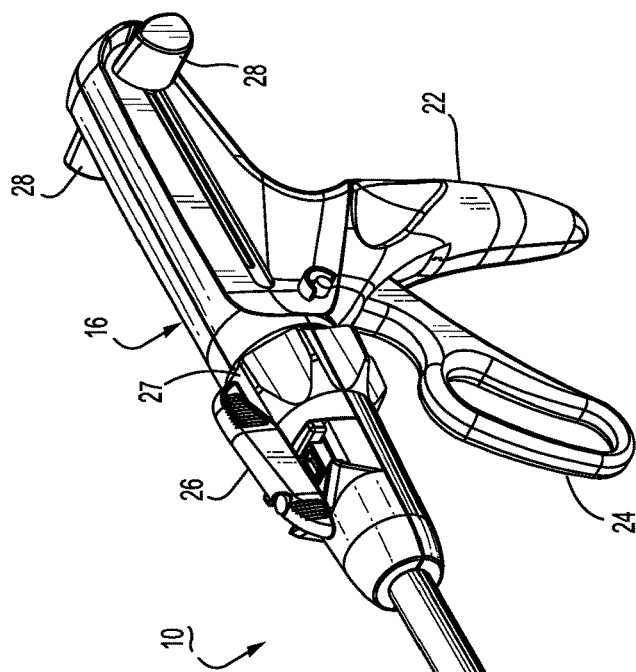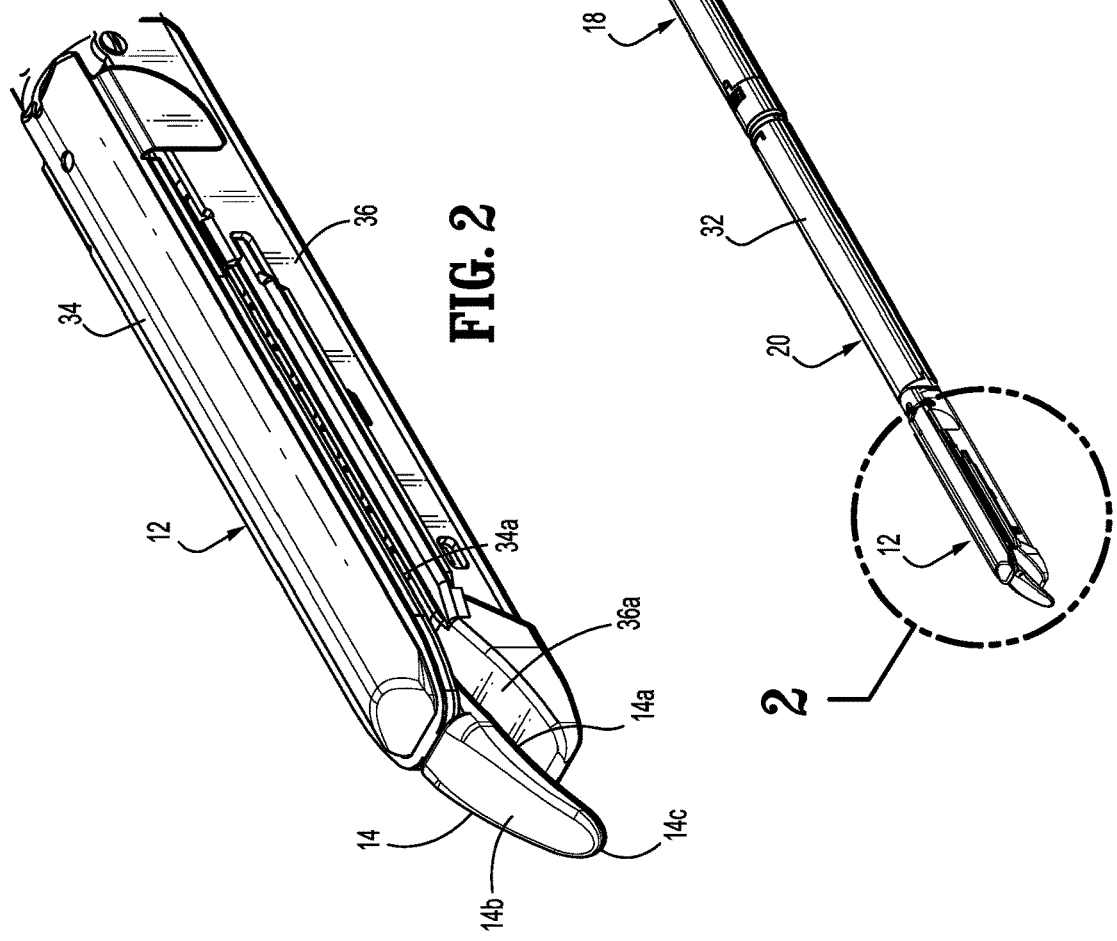

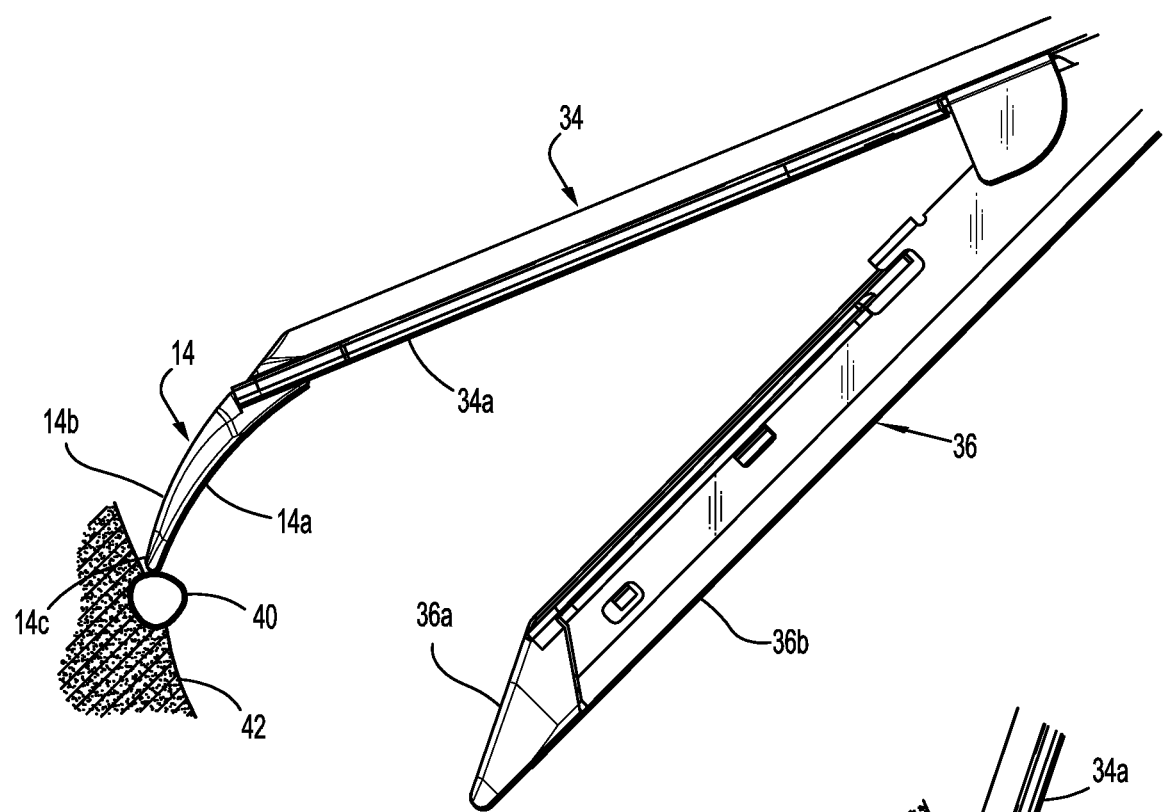
FIG. 3
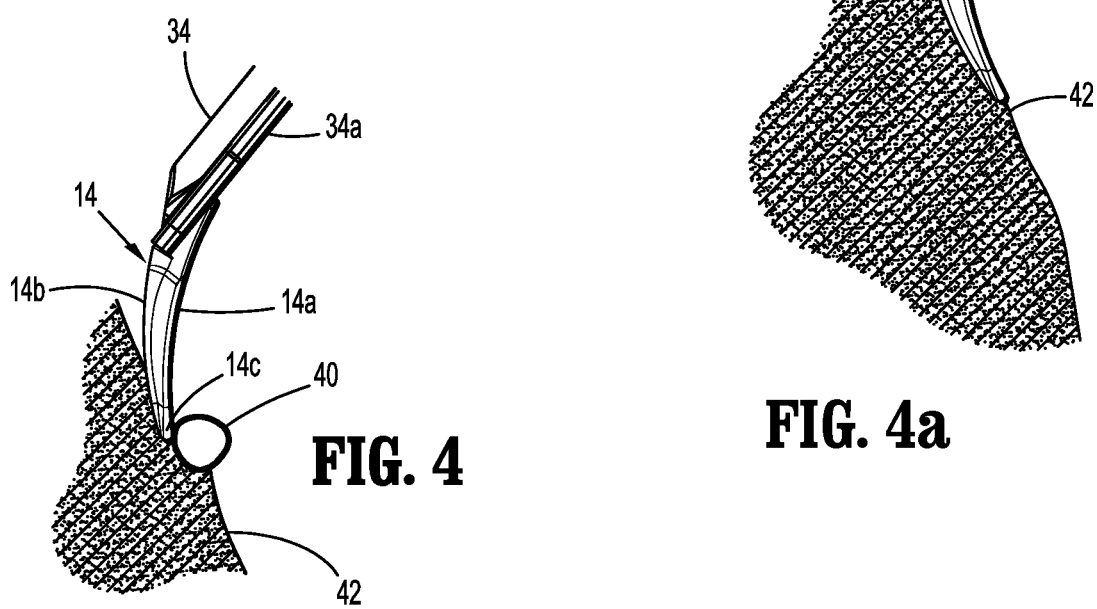
FIG. 4
FIG. 4a

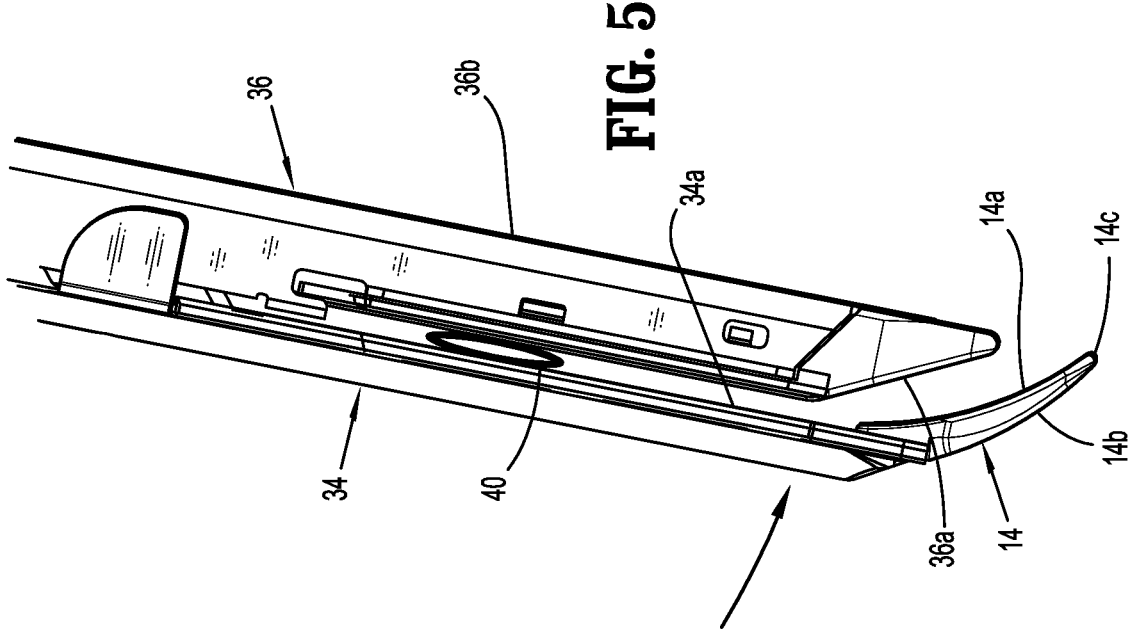
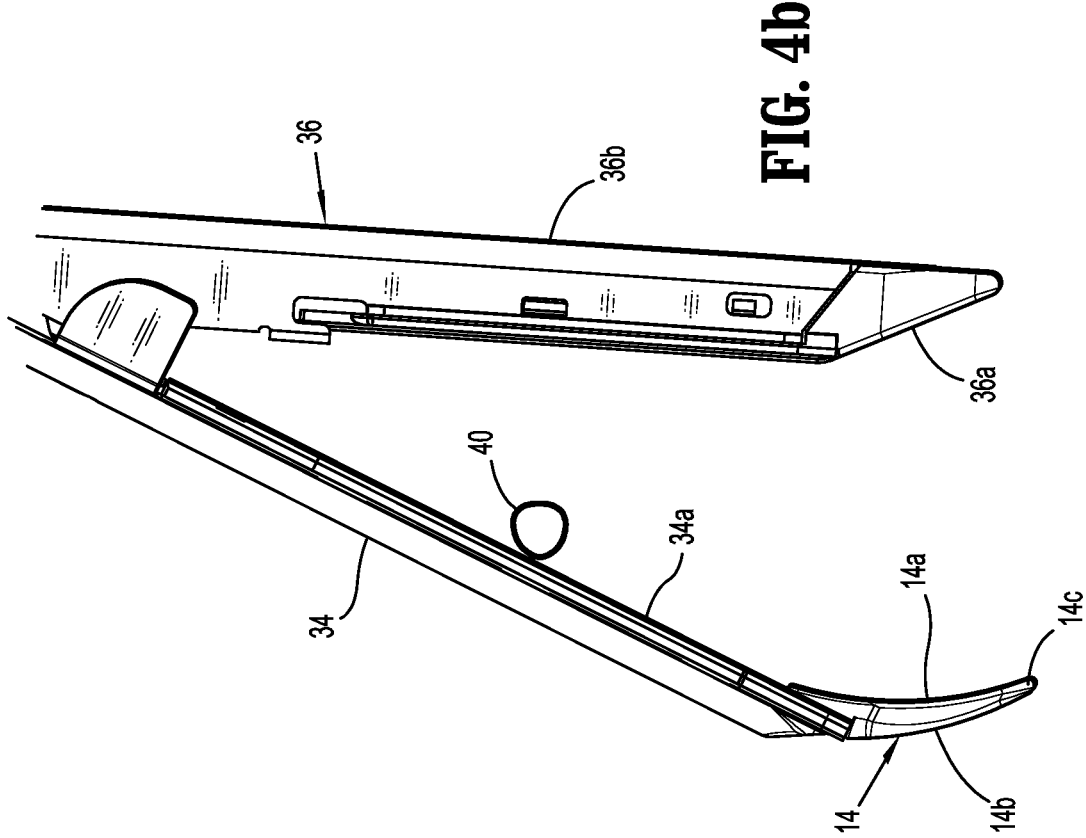

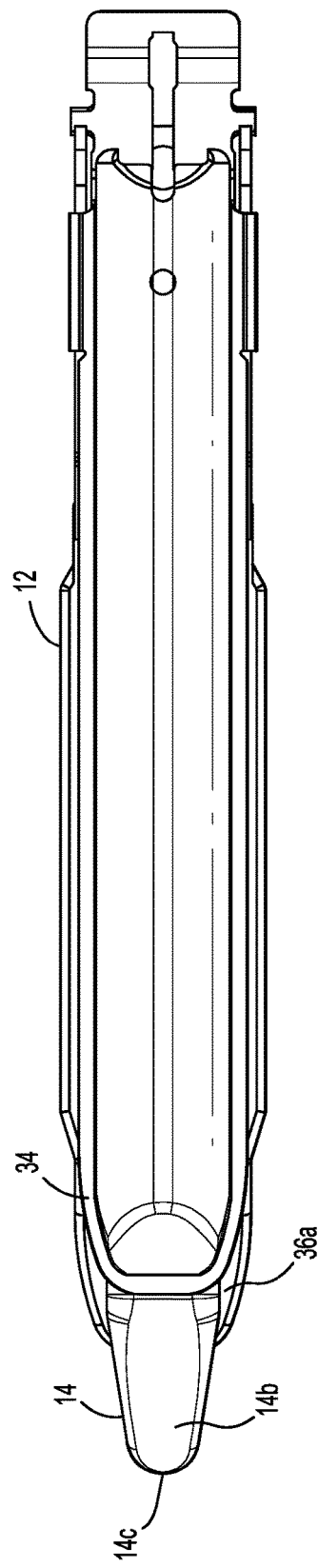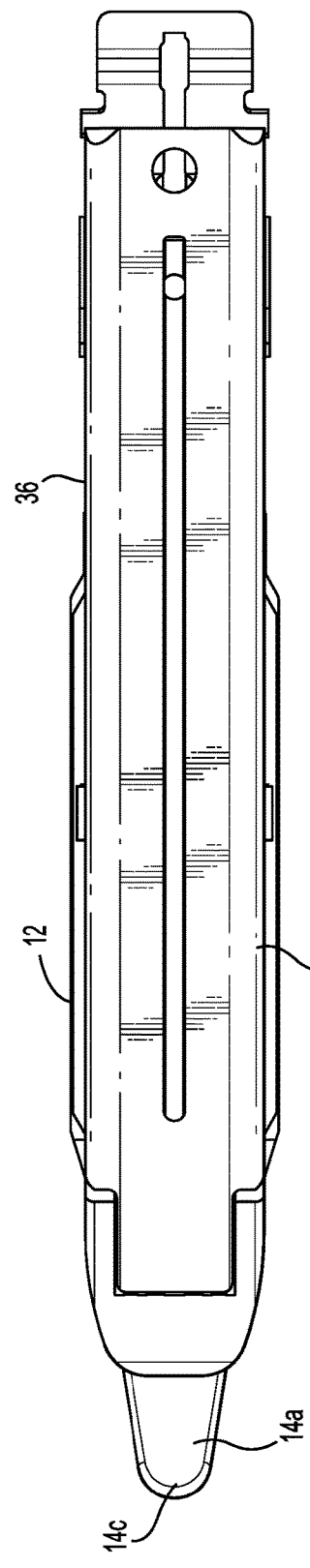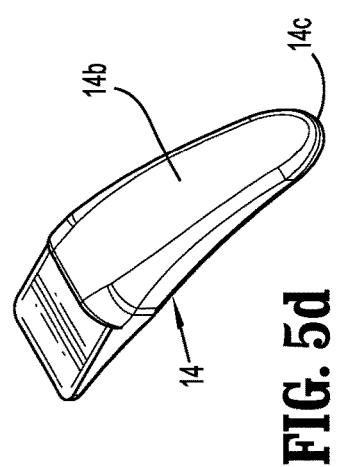
FIG. 5a
FIG. 5b
FIG. 5c
FIG. 5d

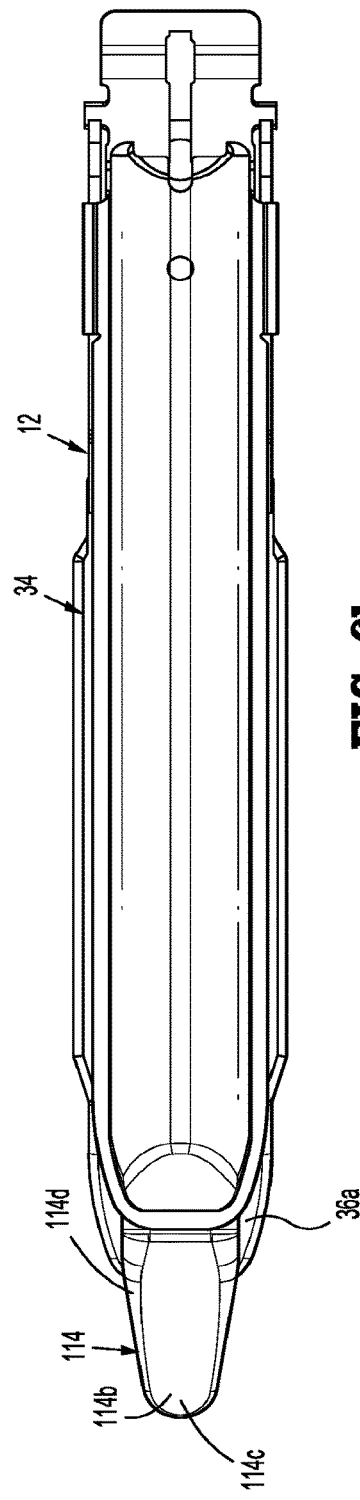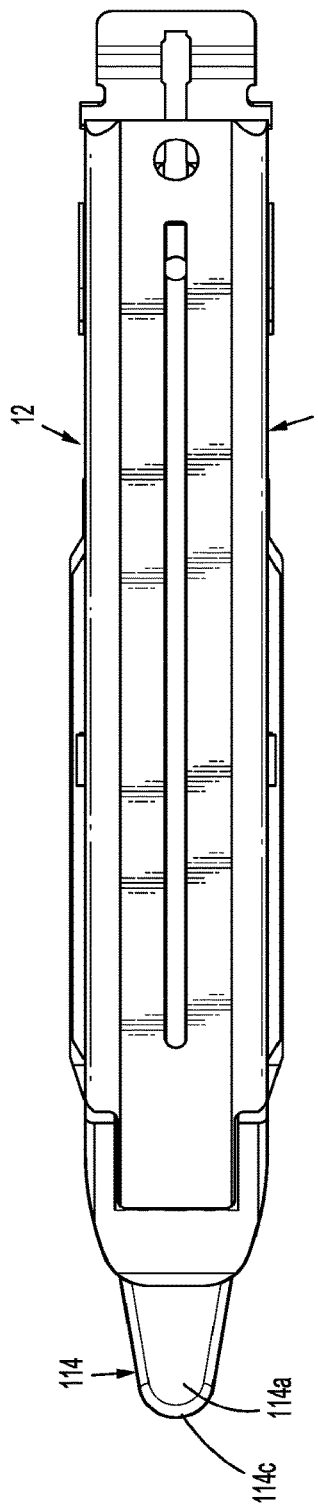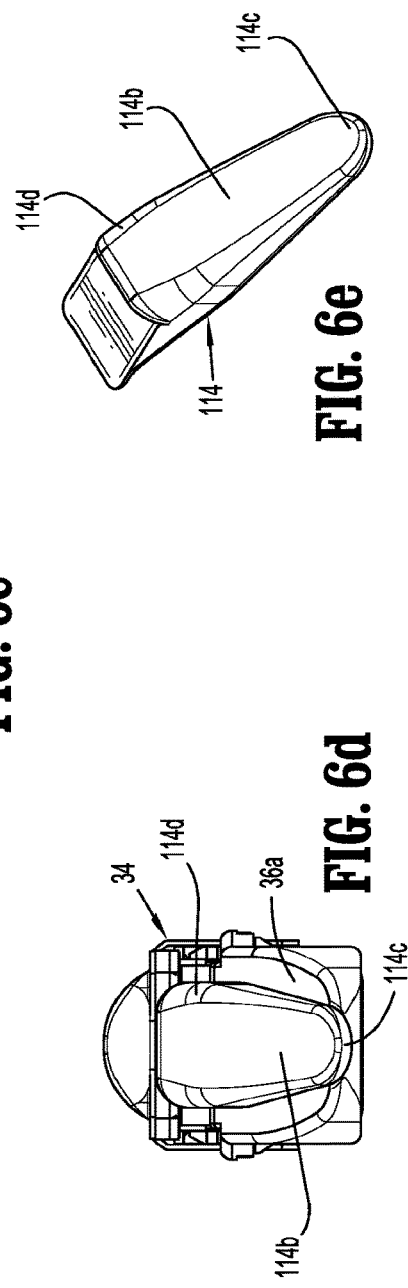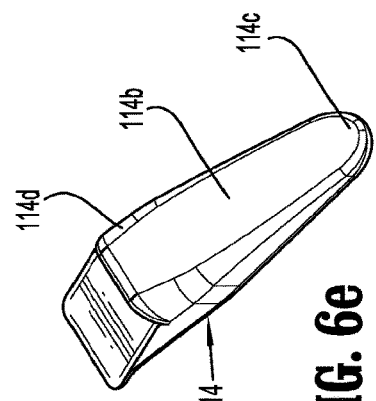
FIG. 6b
FIG. 6c
FIG. 6e
FIG. 6d

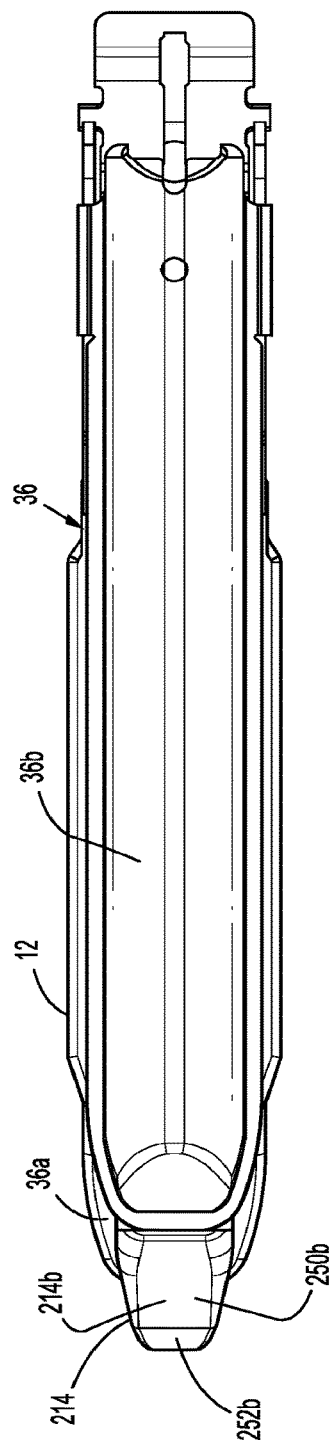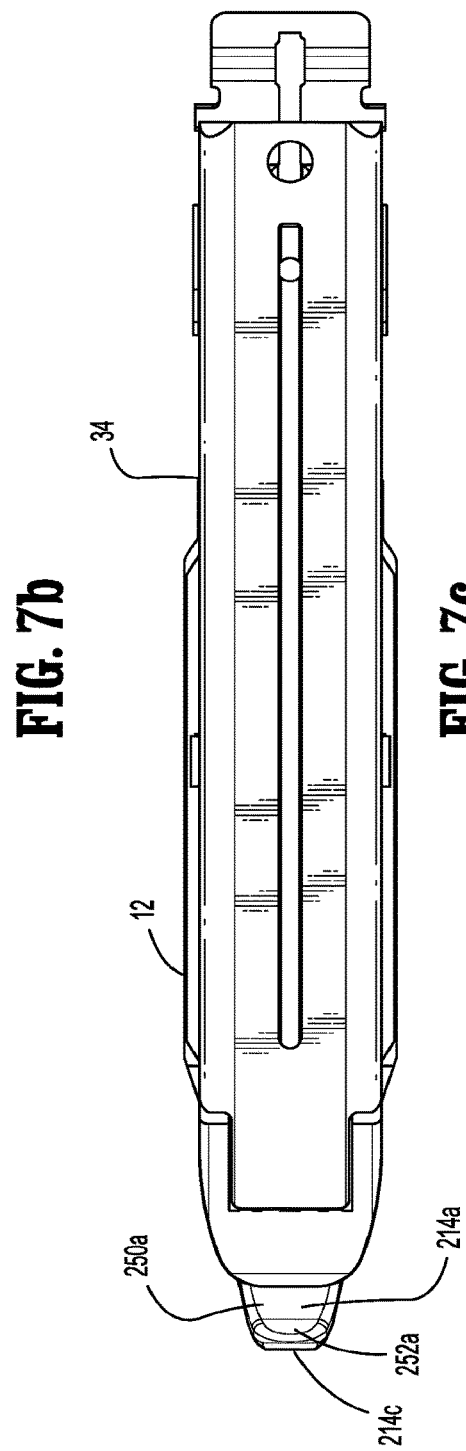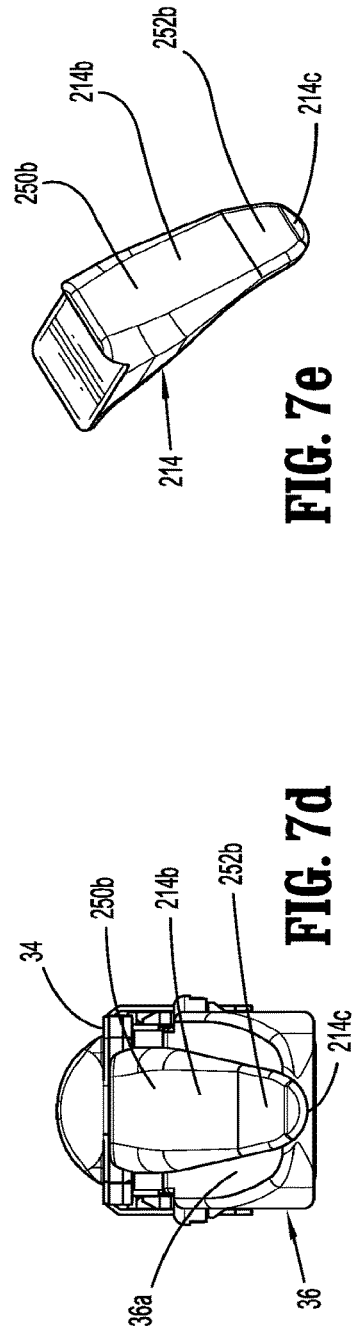

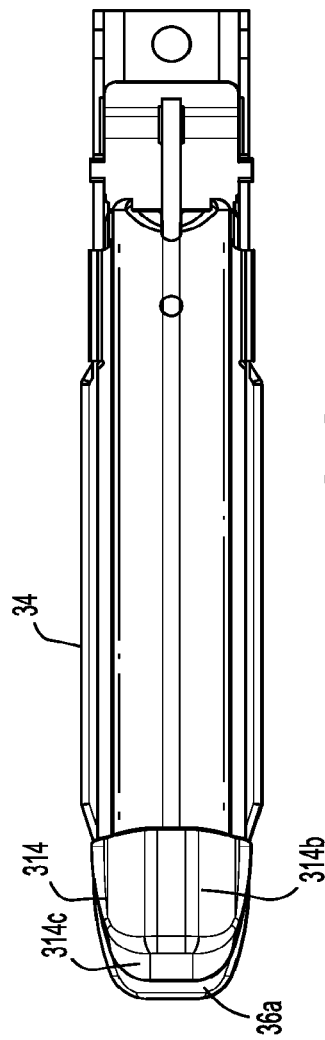
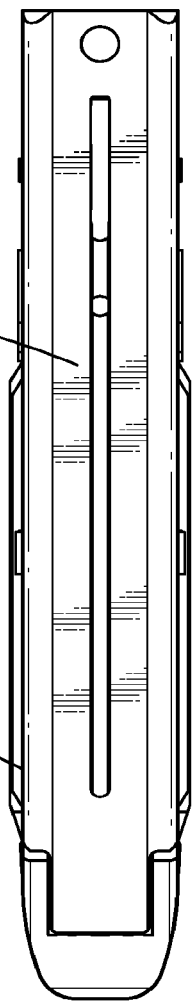
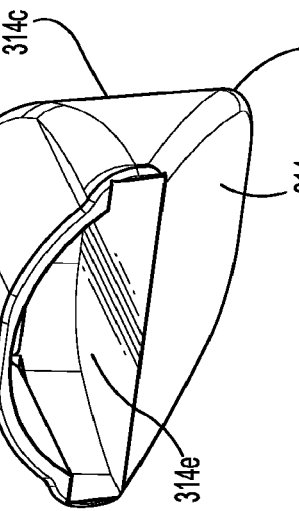
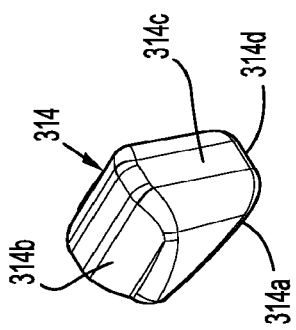
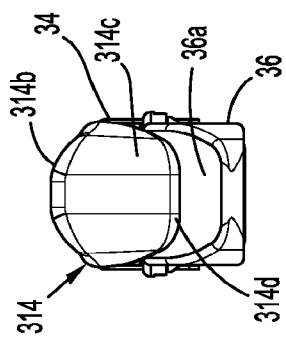

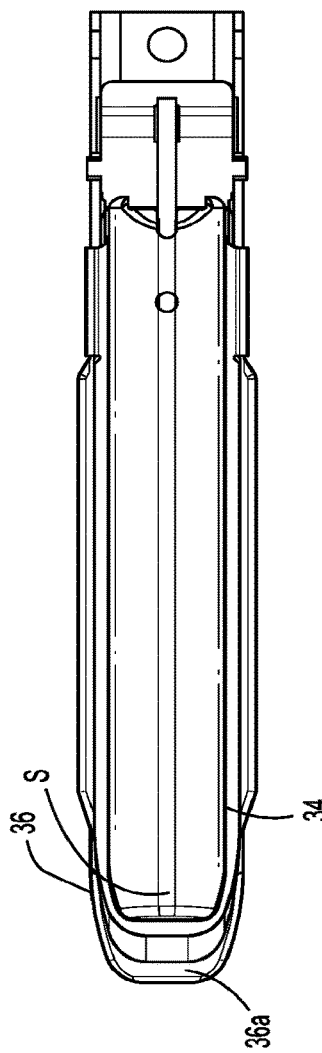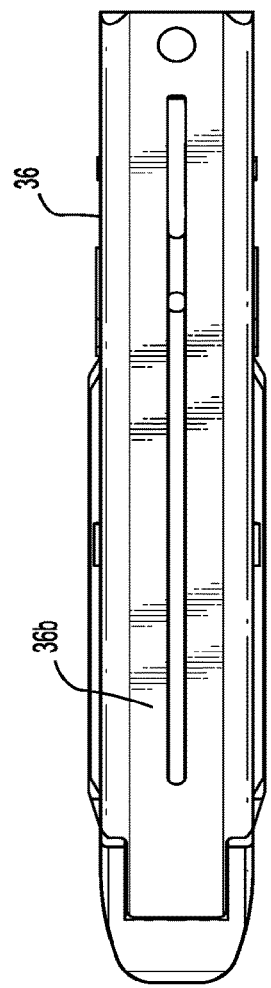

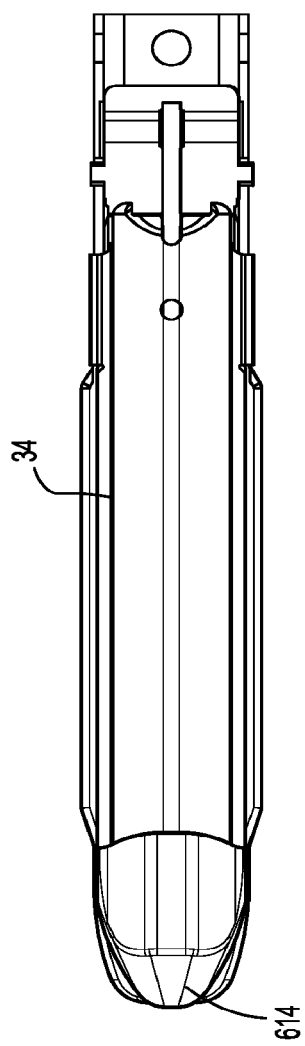
FIG. 11b
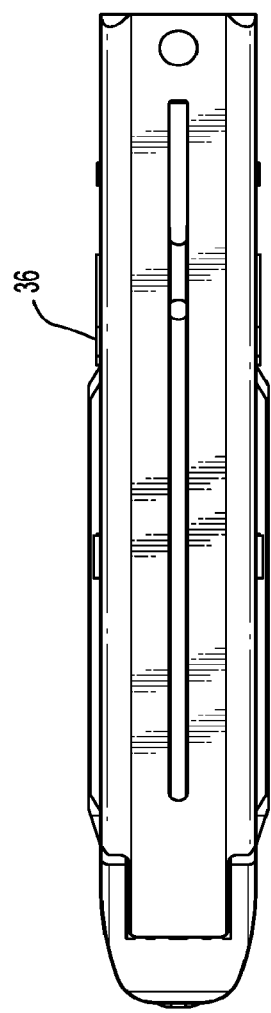
FIG. 11c
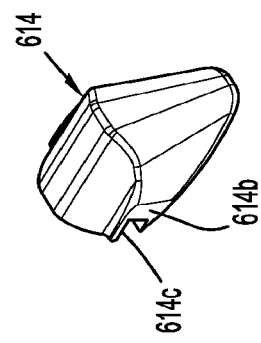
FIG. 11e
FIG. 11d

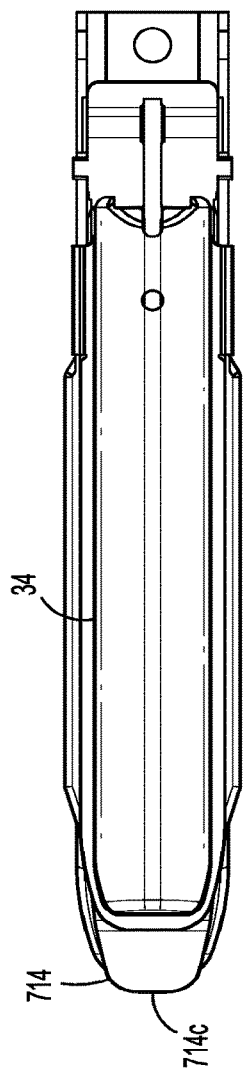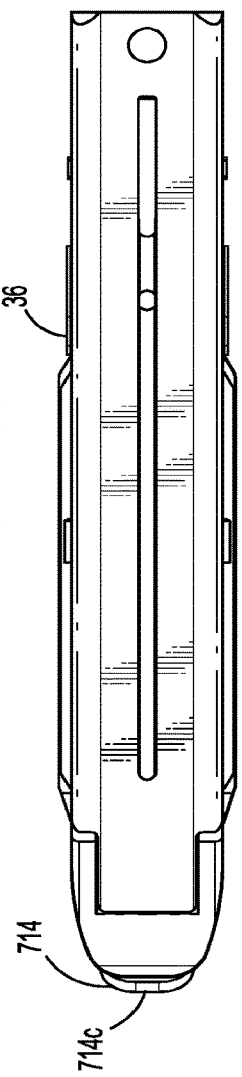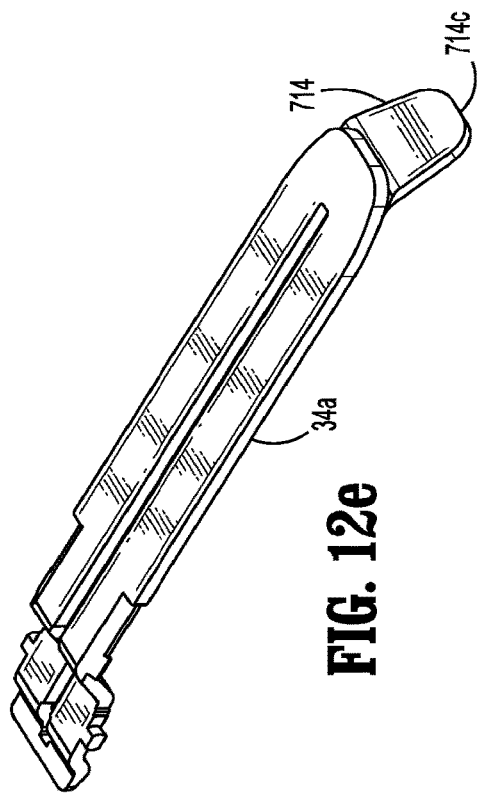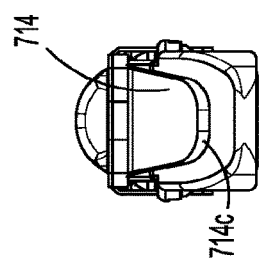
FIG. 12b
FIG. 12c
FIG. 12d
FIG. 12e

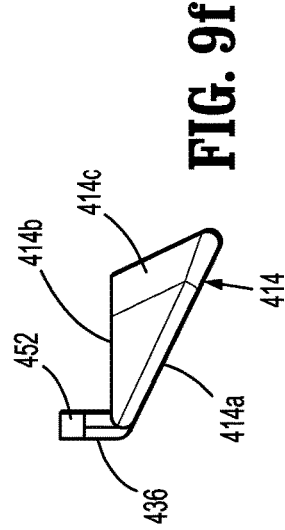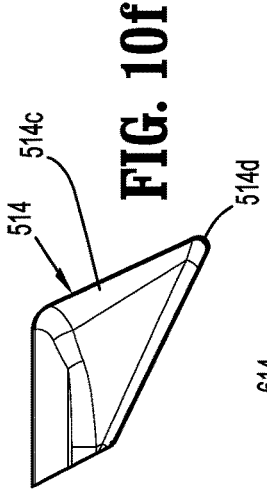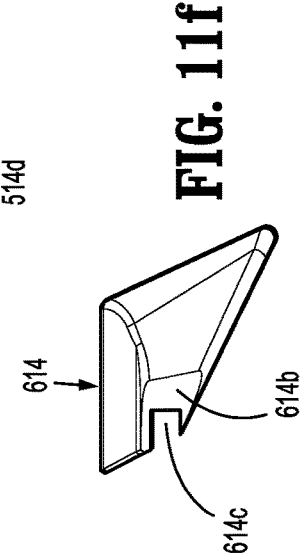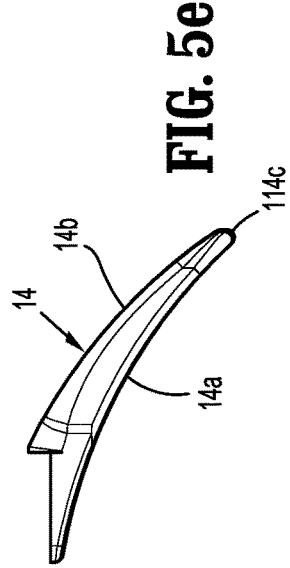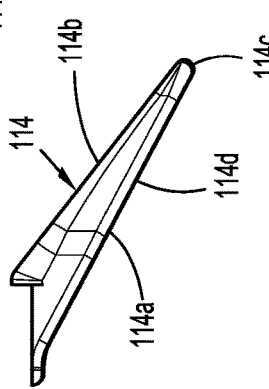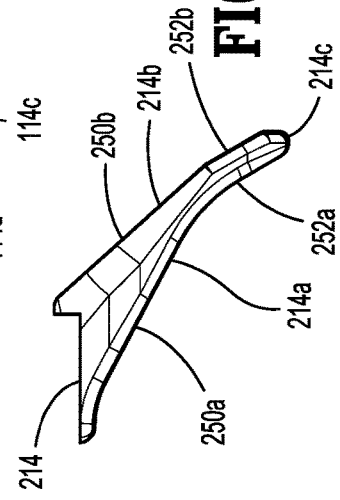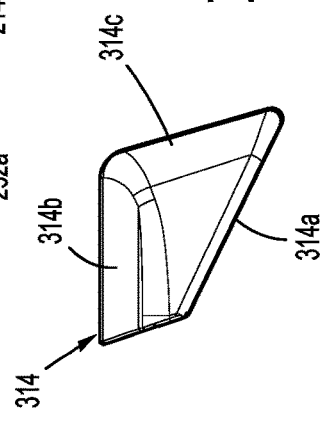

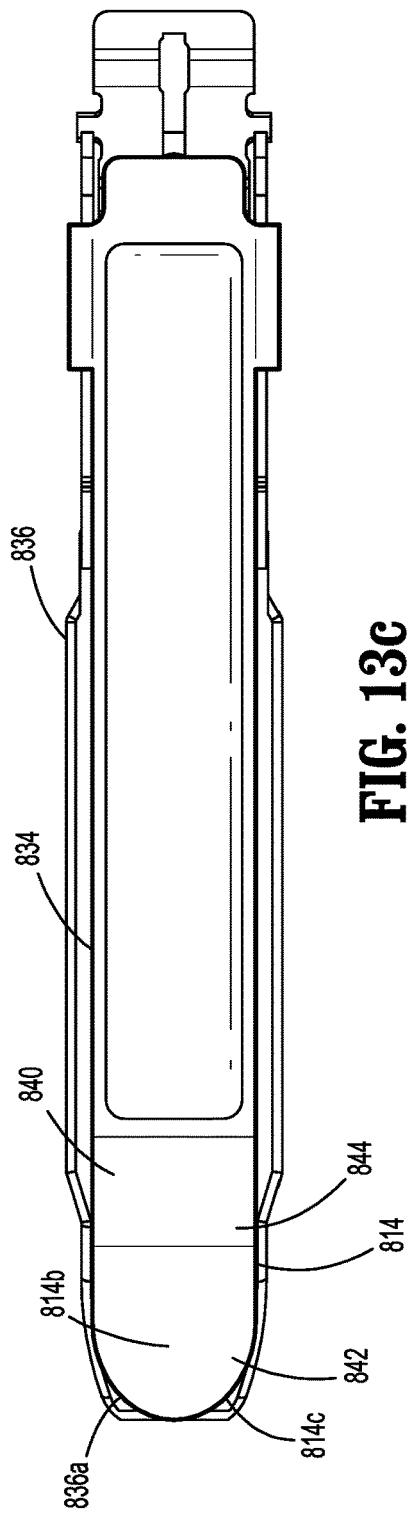
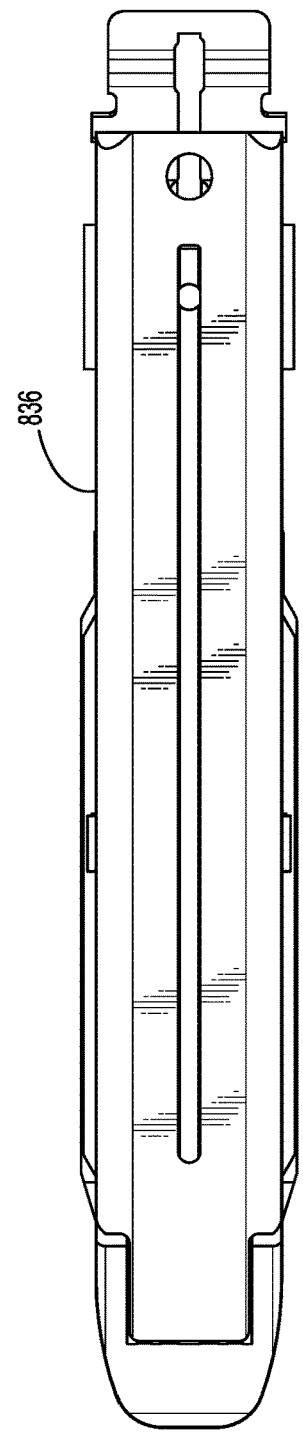
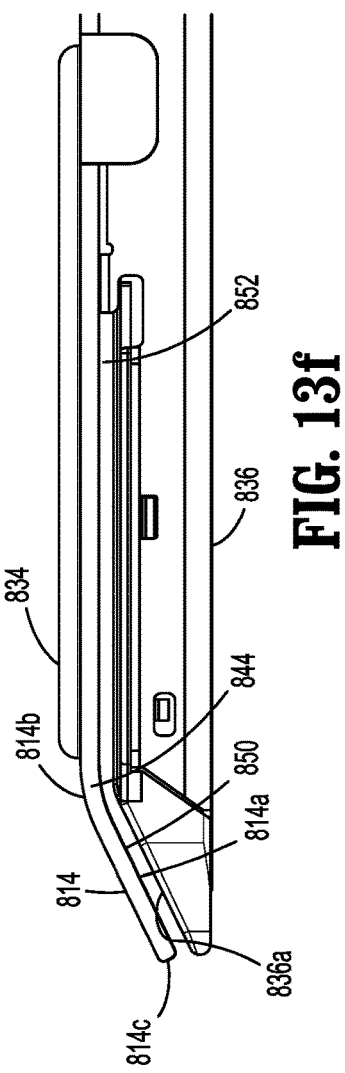
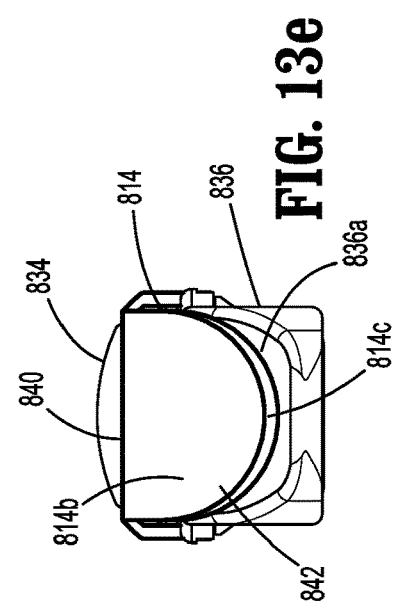
FIG. 13c
FIG. 13d
FIG. 13f
FIG. 13e

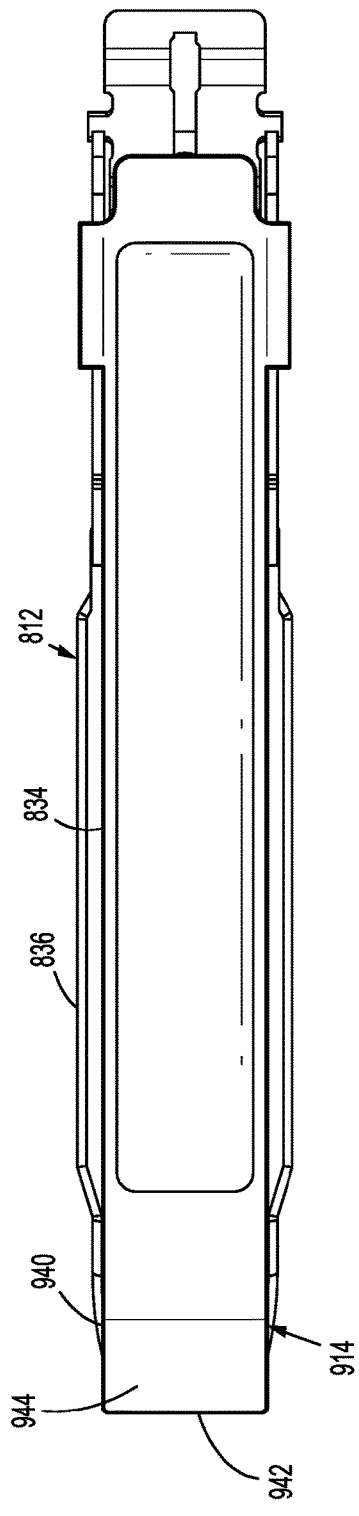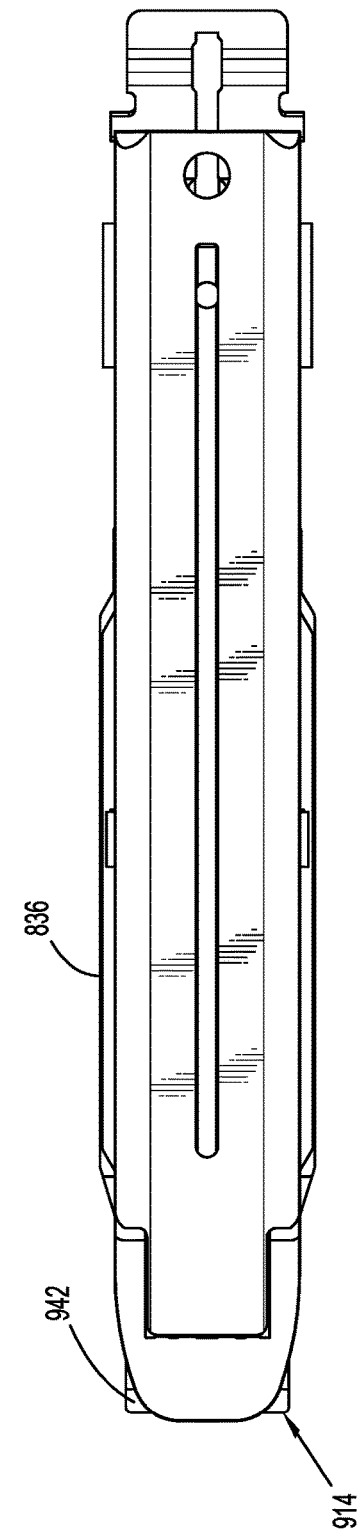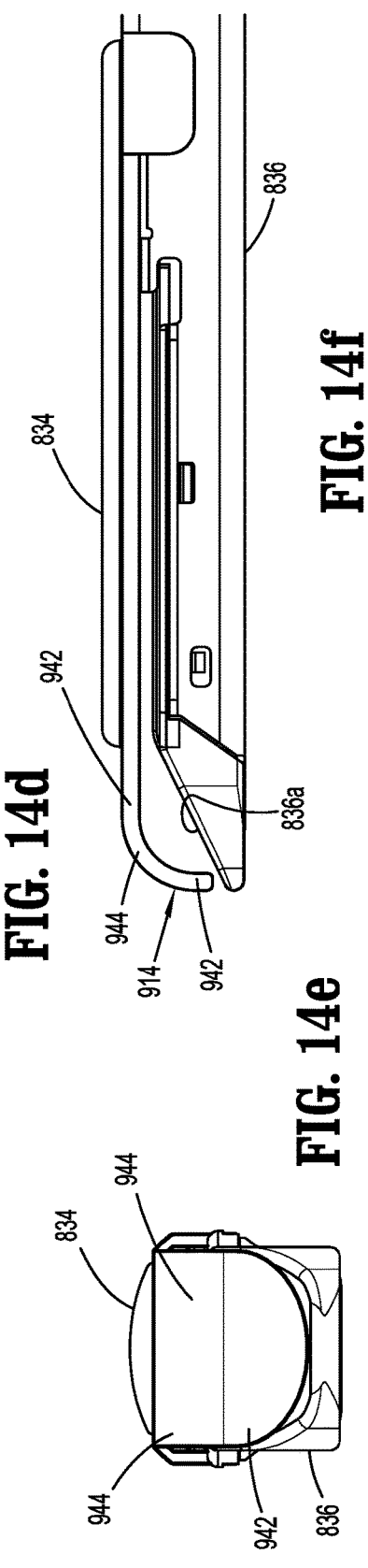

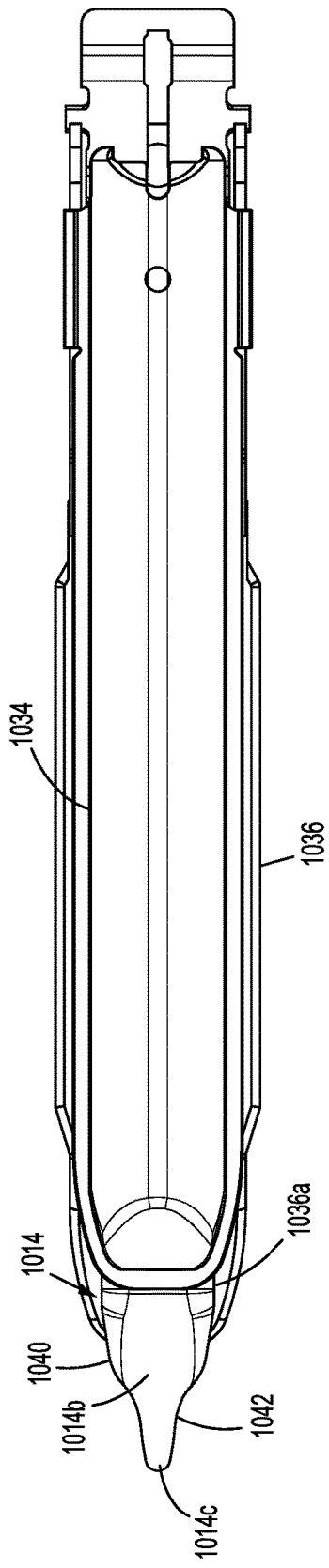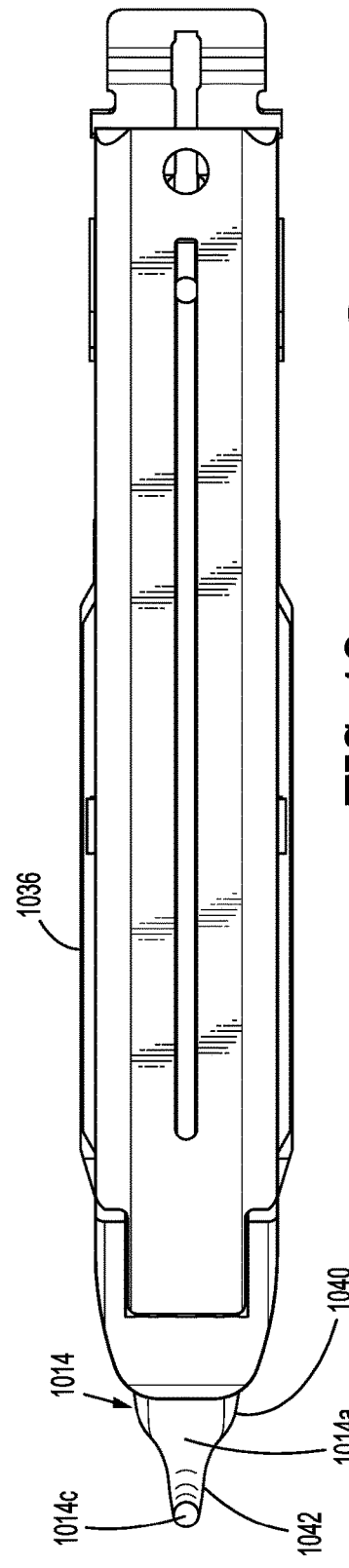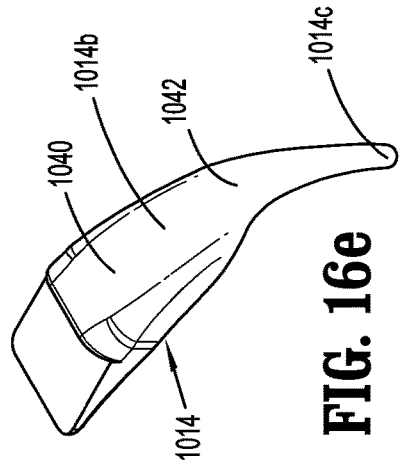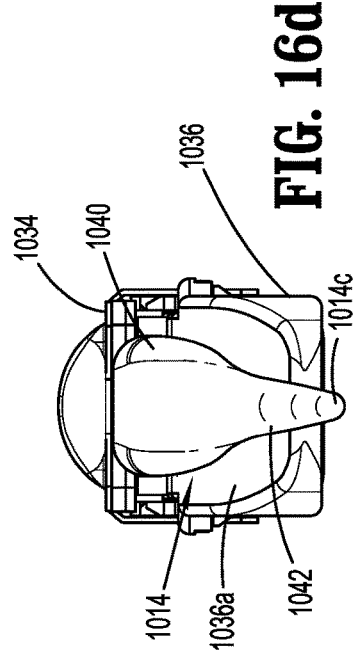
FIG. 16b
FIG. 16c
FIG. 16e
FIG. 16d

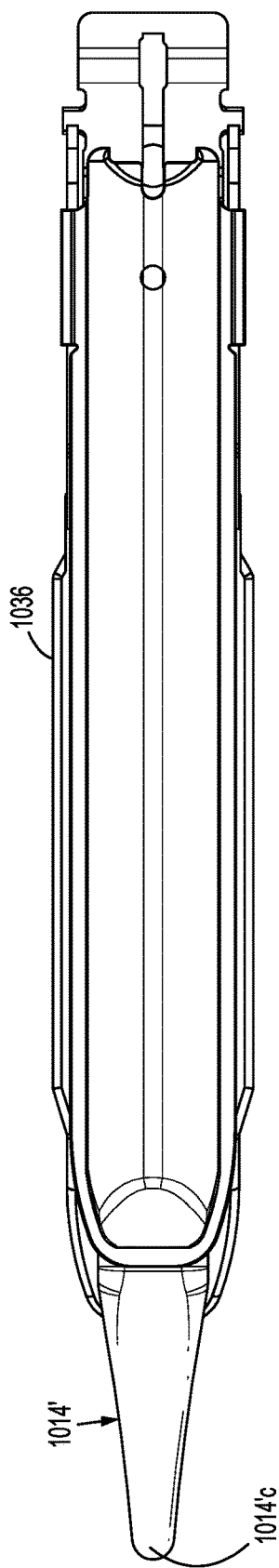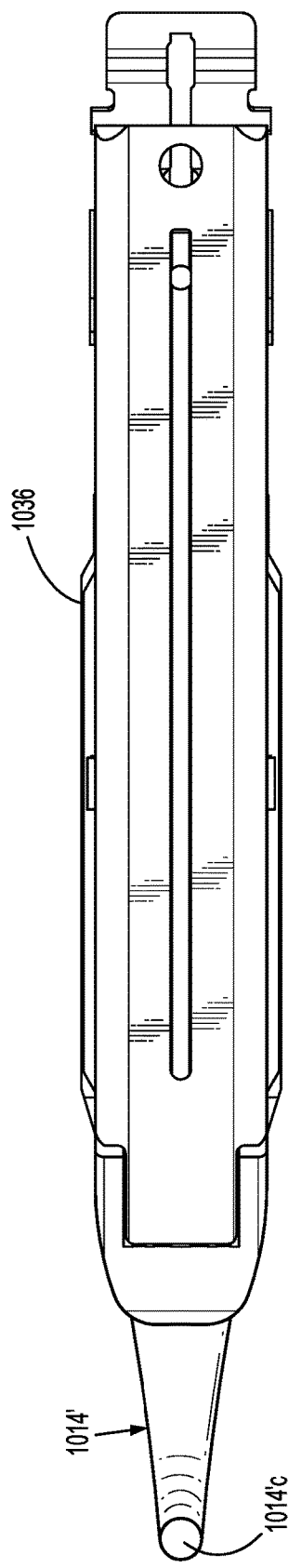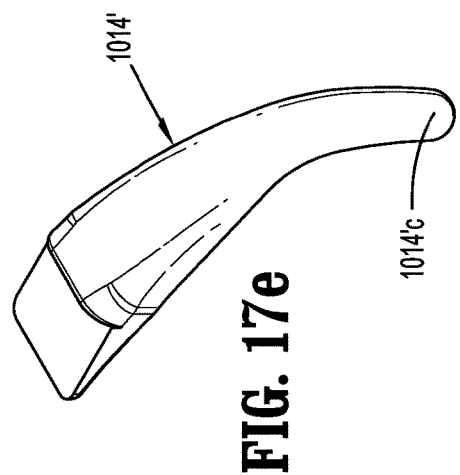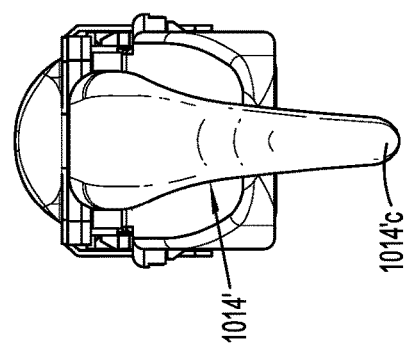
FIG. 17b
FIG. 17c
FIG. 17e
FIG. 17d

SURGICAL STAPLING DEVICE WITH DISSECTING TIP

CROSS-REFERENCE TO RELATED APPLICATIONS

This application is a continuation of U.S. patent application Ser. No. 15/227,482, filed Aug. 3, 2016, which is a continuation of U.S. patent application Ser. No. 11/665,108, filed Jul. 7, 2008, (now U.S. Pat. No. 9,597,078), which claims the benefit of and priority to International Patent Application Serial No. PCT/US2004/013291, filed Apr. 29, 2004, which is Continuation and claims benefit of and priority from U.S. patent application Ser. No. 10/764,103, filed Jan. 23, 2004 (abandoned) and claims benefit of and priority from U.S. Provisional Patent Application No. 60/466,378, filed Apr. 29, 2003, the entire disclosure of which are incorporated by reference herein.

BACKGROUND

Technical Field

This application relates to a surgical stapling device. More particularly, this application relates to a surgical stapling device having an improved tip construction for accessing and/or separating tissue.

Background of Related Art

Surgical staple or fastener applying instruments or devices for joining tissue are well known. Typically, such devices include opposing jaw structure for grasping and clamping selected tissue, wherein one of the jaws of the opposing jaw structure includes a cartridge which houses a plurality of staples or fasteners. In some instruments, a knife is provided to cut tissue which has been joined by the staples or fasteners.

Linear surgical stapling devices, for example, include two elongated members which are relatively moveable to capture or clamp tissue. Typically one of the members includes a cartridge which houses a plurality of staples arranged in two or more linear rows and the other member includes an anvil having a plurality of staple forming pockets for receiving and forming the legs of the staples. Typically, a knife is movably positioned between the linear rows of staples such that when the stapling device is positioned about tissue and actuated, the tissue being joined and/or sealed is simultaneously or nearly simultaneously cut.

Linear surgical stapling devices are commonly used during surgical procedures to simultaneously seal and cut target tissue, e.g., vasculature, organs, etc. It is not uncommon during such procedures that certain tissue, e.g., vasculature or other adherent connective, joined or other tissue, adheres or is joined to the target tissue and must first be separated from the target tissue before the procedure can continue. Currently, a separate device is used to dissect or separate the certain tissue from the target tissue before the target tissue and/or the adherent certain tissue is operated upon. Also, it is a known practice to attach a guide or carrier tube to the distal end of the anvil and to use a separate instrument to pass the tube around the target tissue or structure. The tube is also used to move the back wall of the target tissue into the jaws of the staple device. The tube is removed after the staple is in proper position and then the stapler is fired. These procedures require extra steps and devices and can be time consuming and expensive especially during endoscopic procedures.

Accordingly, a continuing need exists in the art for a device which can be used not only to join and cut tissue but also to separate or dissect certain, e.g., adherent tissue from target tissue. The various embodiments and possible combination of features of the dissecting tips and of the stapling devices and end effectors disclosed herein are advantageous in that they provide dissecting tips or devices mounted or supported on the stapling device, end effector or SULU, therefore which effectively reduce the number of tools needed, reduce the time involved in, and simplify dissection, isolation of target tissue, and stapling procedures. The devices also provide better placement of the stapling device relative to the target tissues. These advantages reduce fatigue of physicians and reduce the cost of the surgical procedures to the hospitals and the patients.

SUMMARY

In accordance with the present disclosure, a dissecting tip is provided for use with a surgical stapling device and, especially, a linear surgical stapling device, including an end effector having an anvil assembly and a cartridge assembly. The stapling device can be configured for open, laparoscopic or endoscopic applications. The dissecting tip is supported on the end effector, and may be supported on the distal end of the anvil assembly. The dissecting tip may instead or also be supported on the distal end of the cartridge assembly. The dissecting tip may be positioned to extend distally from the anvil assembly and includes a body having an outer surface, an inner surface and a distal tip. The body may assume a variety of configurations. For example, the body may include inner and/or outer surfaces which are curved along the longitudinal and/or transverse axis of the anvil assembly and extend downwardly towards the cartridge assembly. In another embodiment, the inner and/or outer surfaces are substantially flat. In yet another embodiment, the inner and/or outer surfaces include a pair of flat sections interconnected by a curved transition section. In yet another embodiment, the body may include a distal portion having a distal tip having an oblong, oval and/or circular cross-section. The width of the dissecting tip may decrease or increase from the proximal end of the dissecting tip to the distal end of the dissecting tip. The distal tip of the dissecting tip may also be "rounded" and/or blunt to prevent snagging, pulling and/or cutting of tissue.

The dissecting tip functions to dissect or separate target tissue and certain tissue. As discussed above, "certain tissue" includes adherent, connective, joined or other tissue. This may be accomplished by passing or pressing the outer surface of dissecting tip against the target tissue and pushing the distal tip of the dissecting tip behind the certain tissue such that the certain tissue is positioned adjacent the inner surface of the dissecting tip. The dissecting tip may be located and dimensioned to permit access through a trocar cannula assembly which is sized to receive a surgical stapling instrument without a dissecting tip.

In one aspect of the invention, it is advantageous to provide a dissection tip for use with a surgical stapler, the dissecting tip comprising a proximal portion configured to be fastened or attached to an end effector, desirably to an anvil assembly of the end effector, a distal portion contiguous or in communication with the proximal portion, the distal portion having an inner surface that has a planar portion, the anvil assembly having a longitudinal axis that can be along the tissue contacting surface of the anvil assembly, and the planar surface being disposed at an angle relative to the horizontal axis. The angle can be any suitable angle, e.g., from about 50 to about 90.degree., more desirably from about 30.degree. to about 90.degree., and most desirably about or close to 90.degree., relative to the longitudinal axis. In another aspect of the invention for some applications, it is advantageous to provide a final angular orientation of the distal portion of the dissecting tip by or about 30-45.degree.

In another aspect of the invention, it is advantageous that the dissecting tip have a planar angular distal surface, that faces toward the planar angular distal guide surface of the cartridge assembly when the cartridge and anvil assemblies are in a clamped or closed position.

In another aspect of the invention, it is advantageous that the planar angular surface of the cartridge assembly distal end be uninterrupted, and further advantageous that the planar inner surface of the dissecting tip and the planar angular surface of the cartridge assembly be spaced from each other when the anvil and cartridge assemblies are in the closed or clamped position.

In another aspect of the invention, it is advantageous to provide surgical stapling instruments that incorporate or have fastened thereto other types of vascular dissecting instruments. These would provide one or more of the advantageous effects herein disclosed.

In yet another aspect of the invention, it is advantageous to provide a dissecting tip for use with a surgical stapler or instrument comprising a body having a proximal portion configured to receive and engage a distal end of an end effector of a surgical stapler or instrument and a distal portion having a substantially flat inner surface and a substantially flat outer surface wherein the flat inner surface and flat outer surface are configured at an angle of from about 5.degree. to about 90.degree. to a longitudinal axis of the anvil assembly. By providing such a dissecting tip body, certain tissue can be separated and/or dissected from target tissue using the surgical stapler or instrument.

In another aspect of the invention, it is advantageous to provide a dissecting tip for use with a surgical stapler or instrument comprising a proximal portion configured for receipt and attachment to a distal end of an end effector of a surgical stapler; a distal portion having a curved inner surface and a curved outer surface; and a distal tip, wherein the dissecting tip has a width which decreases substantially continuously from the proximal portion to the distal tip or from a location proximal of the distal tip to the distal tip. By providing a reduced width at the distal tip, visibility to a surgeon at the site of dissection or separation is improved.

In yet another aspect of the invention, it is advantageous to provide an end effector comprising an anvil assembly including a dissecting tip, wherein the dissecting tip comprises a proximal portion configured to receive and engage a distal end of the anvil assembly; a distal portion having an inner surface and an outer surface; and a distal tip; and a cartridge assembly having a distal end, wherein the distal tip extends beyond the distal end of the cartridge assembly. By providing a distal tip which extends beyond the distal end of the cartridge assembly, visibility is improved and dissection can occur with the end effector in the clamped position.

In yet another aspect of the invention, it is advantageous to provide an end effector comprising an anvil assembly having a dissecting tip extending therefrom; and a cartridge assembly having an uninterrupted tissue guide surface formed on a distal end thereof, wherein the dissecting tip is positioned above the distal guide surface of the cartridge assembly to define a gap therebetween. By providing an uninterrupted guide surface on the cartridge assembly which defines a gap with the dissecting tip, compression and traumatization of tissue at the distal end of the end effector can be minimized.

BRIEF DESCRIPTION OF THE DRAWINGS

Various embodiments of the presently disclosed dissecting tip are described herein with reference to the drawings, wherein:

FIG. 1 is a side top perspective view of a surgical stapling device including one embodiment of the presently disclosed dissecting tip attached to the end effector thereof;

FIG. 2 is an enlarged view of the indicated area of detail shown in FIG. 1;

FIG. 3 is a side view of the end effector with portions broken away and of the dissecting tip of the surgical stapling device shown in FIG. 1 with the end effector in the open position adjacent target tissue and certain tissue which is adhered to the target tissue;

FIG. 4 is a side view of the anvil assembly shown in FIG. 3 with the dissecting tip positioned partially between the certain tissue and the target tissue;

FIG. 4a is a side view of the anvil assembly and dissecting tip shown in FIG. 4 positioned fully between the certain tissue and the target tissue;

FIG. 4b is a side view of the dissecting tip and end effector shown in FIG. 3 with certain tissue positioned between an open anvil assembly and cartridge assembly;

FIG. 5 is a side view of the dissecting tip and end effector shown in FIG. 4b with certain tissue positioned between a clamped anvil assembly and cartridge assembly;

FIG. 5a is a top view of the dissecting tip and end effector of the surgical stapling device shown in FIG. 1;

FIG. 5b is a bottom view of the dissecting tip and end effector shown in FIG. 5a;

FIG. 5c is a front view of the dissecting tip and end effector shown in FIG. 5b;

FIG. 5d is a side perspective view from the front of the presently disclosed dissecting tip dissector shown in FIG. 1;

FIG. 5e is a side view of the dissecting tip shown in FIG. 5d;

FIG. 6b is a top view of the dissecting tip and end effector of the surgical stapling device shown in FIG. 6;

FIG. 6c is a bottom view of the dissecting tip and end effector shown in FIG. 6b;

FIG. 6d is a front view of the dissecting tip and end effector shown in FIG. 6c;

FIG. 6e is a side top perspective view from the front of the presently disclosed dissecting tip shown in FIG. 6;

FIG. 6f is a side view of the dissecting tip shown in FIG. 6e;

FIG. 7b is a top view of the dissecting tip and end effector of the surgical stapling device shown in FIG. 7;

FIG. 7c is a bottom view of the dissecting tip and end effector shown in FIG. 7b;

FIG. 7d is a front view of the dissecting tip and end effector shown in FIG. 7c;

FIG. 7e is a side top perspective view from the front of the presently disclosed dissecting tip shown in FIG. 7;

FIG. 7f is a side view of the dissecting tip shown in FIG. 7e;

FIG. 8b is a top view of the dissecting tip and end effector of the surgical stapling device shown in FIG. 8;

FIG. 8c is a bottom view of the dissecting tip and end effector shown in FIG. 8b;

FIG. 8d is a front view of the dissecting tip and end effector shown in FIG. 8c;

FIG. 8e is a side perspective view from the front of the presently disclosed dissecting tip shown in FIG. 8;

FIG. 8f is a side perspective view from the rear of the dissecting tip shown in FIG. 8e;

FIG. 8g is a side view of the dissecting tip shown in FIG. 8e;

FIG. 9b is a top view of the dissecting tip and end effector of the surgical stapling device shown in FIG. 9;

FIG. 9c is a bottom view of the dissecting tip and end effector shown in FIG. 9b;

FIG. 9d is a front view of the dissecting tip and end effector shown in FIG. 9c;

FIG. 9e is a side perspective view from the front of the presently disclosed dissecting tip shown in FIG. 9;

FIG. 9f is a side view of the dissecting tip shown in FIG. 9e;

FIG. 10f is a side view of the dissecting tip shown in FIG. 10e;

FIG. 11b is a top view of the dissecting tip and end effector of the surgical stapling device shown in FIG. 11;

FIG. 11c is a bottom view of the dissecting tip and end effector shown in FIG. 11b;

FIG. 11d is a front view of the dissecting tip and end effector shown in FIG. 11c;

FIG. 11e is a side perspective view from the front of the presently disclosed dissecting tip shown in FIG. 11;

FIG. 11f is a side view of the dissecting tip shown in FIG. 11e;

FIG. 12b is a top view of the dissecting tip and end effector of the surgical stapling device shown in FIG. 12;

FIG. 12c is a bottom view of the dissecting tip and end effector shown in FIG. 12b;

FIG. 12d is a front view of the dissecting tip and end effector shown in FIG. 12c;

FIG. 12e is a side perspective view from the front of the presently disclosed dissecting tip shown in FIG. 12;

FIG. 12f is a side view of the dissecting tip shown in FIG. 12e;

FIG. 13c is a top view of the end effector and dissecting tip shown in FIG. 13a;

FIG. 13d is a bottom view of the end effector and dissecting tip shown in FIG. 13a;

FIG. 13e is a front view of the end effector and dissecting tip shown in FIG. 13a;

FIG. 13f is a side view of the end effector and dissecting tip shown in FIG. 13a;

FIG. 14c is a top view of the end effector and dissecting tip shown in FIG. 14a;

FIG. 14d is a bottom view of the end effector and dissecting tip shown in FIG. 14a;

FIG. 14e is a front view of the end effector and dissecting tip shown in FIG. 14a;

FIG. 14f is a side view of the end effector and dissecting tip shown in FIG. 14a;

FIG. 16b is a top view of the end effector and dissecting tip shown in FIG. 16a;

FIG. 16c is a bottom view of the end effector and dissecting tip shown in FIG. 16a;

FIG. 16d is a front view of the end effector and dissecting tip shown in FIG. 16a;

FIG. 16e is a side perspective view from above of the dissecting tip shown in FIG. 16a;

FIG. 17b is a top view of the end effector and dissecting tip shown in FIG. 17a;

FIG. 17c is a bottom view of the end effector and dissecting tip shown in FIG. 17a;

FIG. 17d is a front view of the end effector and dissecting tip shown in FIG. 17a; and FIG. 17e is a side perspective view from above of the dissecting tip shown in FIG. 17a.

DETAILED DESCRIPTION OF EMBODIMENTS

Figure 6:
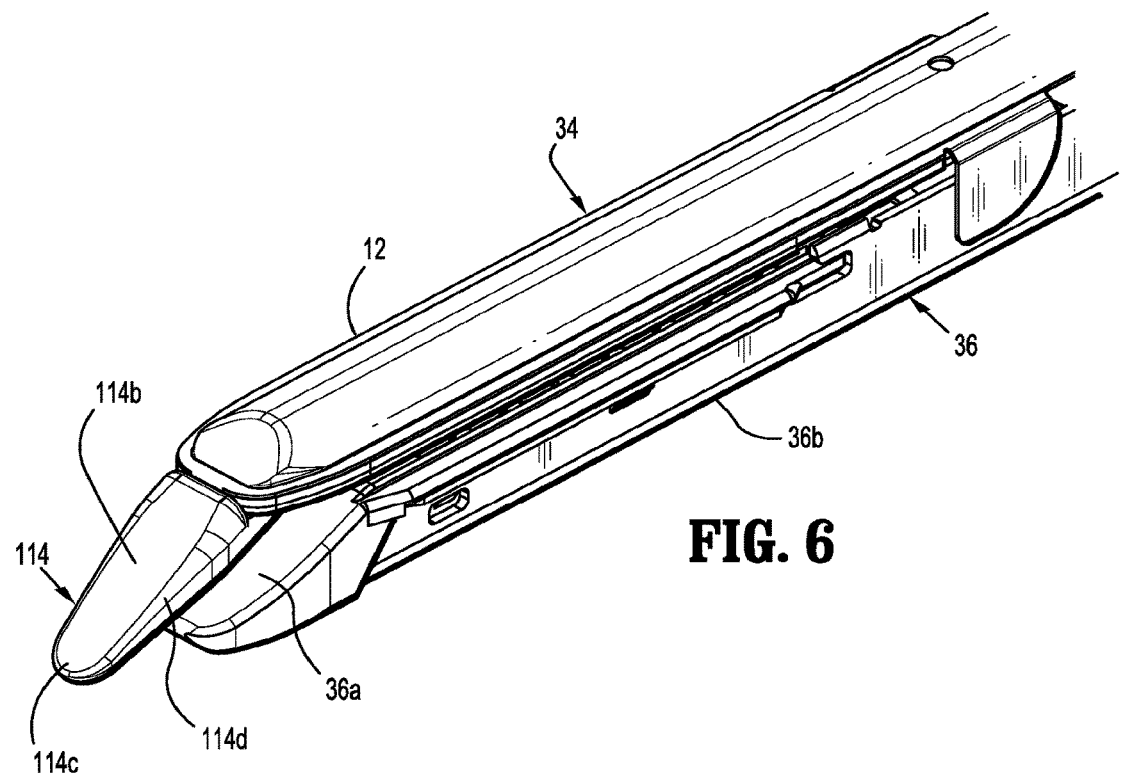
FIG. 6 is an enlarged top side perspective view from the front of the end effector of a surgical stapling device including another embodiment of the presently disclosed dissecting tip.
Figure 6A:
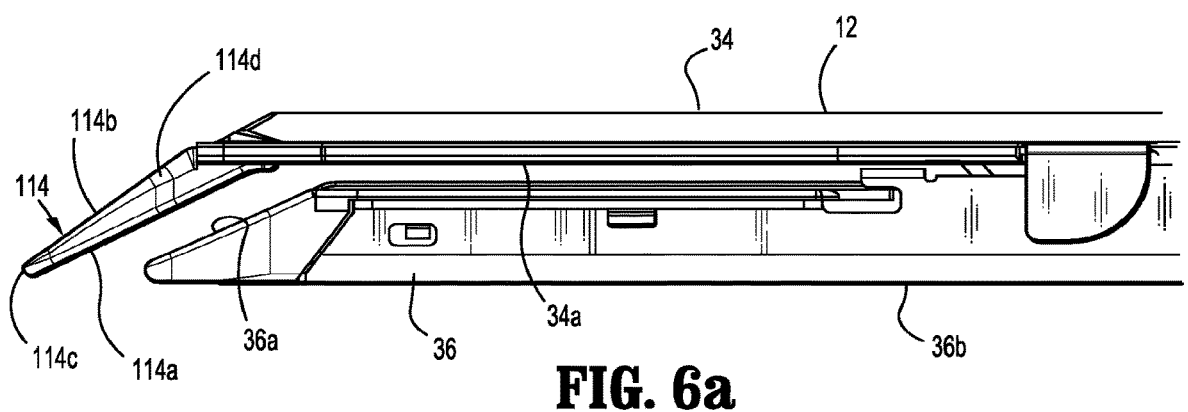
FIG. 6a is a side view of the dissecting tip and end effector shown in FIG. 6.

Embodiments of the presently disclosed surgical stapling device with dissecting tip will now be described in detail with reference to the drawings wherein like reference numerals designate identical or corresponding elements in each of the several views.

In the description that follows, the term "proximal", as is traditional, will refer to the end of the stapling device closest the operator and the term "distal" will refer to the end of the stapling device furthest from the operator.

FIG. 1 illustrates a linear surgical stapling device shown generally as 10 including an end effector 12 having one embodiment of the presently disclosed dissecting tip, here generally designated 14, supported thereon. Stapling device 10 also includes a handle assembly 16 and an endoscopic portion 18. End effector 12 forms part of a disposable loading unit or single use loading unit (SULU) 20. With the exception of dissecting tip 14, the remaining components of surgical stapling device 10 are substantially as known in the art described in U.S. Pat. No. 5,865,361 ("'361 patent"), U.S. Pat. Nos. 6,079,606, 6,241,139, 6,330,965 and 6,669,073. It is contemplated that the presently disclosed embodiments of the dissecting tip may be used in association with other known linear stapling devices of both endoscopic and open construction. These devices include articulating and non-articulating devices as well as reusable and non-reusable devices. Examples of such devices are disclosed in U.S. Pat. Nos. 6,202,914, 6,250,532, 6,109,500, 6,032,849, 5,584,425, 5,540,375, 5,554,169, 5,507,426, 5,482,197. In light of the comments above, only the embodiments of the dissecting tips disclosed herein will be discussed in detail in this application.

FIGS. 1-5c illustrate one embodiment of the presently disclosed dissecting tip in combination with a surgical stapling device 10. As discussed above, surgical stapling device 10 includes a handle assembly 16, an elongated body or endoscopic portion 18, and in this embodiment a SULU 20. It is contemplated that the end effectors of the embodiments disclosed herein may form a permanent part of the stapling device. Briefly, handle assembly 16 includes a stationary grip member 22, a pivotable trigger 24, an articulation lever 26, a rotation knob 27 and return knobs 28. SULU 20 is adapted to be releasably attached to elongated body portion 18 and includes a proximal body portion 32 and end effector 12. End effector 12 is pivotally attached to proximal body portion 32 to facilitate articulation of end effector 12 in relation to proximal body portion 32.

End effector 12 includes an anvil assembly 34 and a cartridge assembly 36 which houses a plurality of linear rows of staples. Anvil assembly 34 and cartridge assembly 36 are movable, here, pivotal in relation to each other between an open position and a clamped or approximated position. Pivotable trigger 24 is actuable through an actuation stroke or strokes to move anvil assembly 34 in relation to cartridge assembly 36 between the open position and the clamped position and to eject staples from cartridge assembly 36. The operation of each of these components is described in greater detail in the '361 patent and will not be discussed in further detail herein.

Dissecting tip 14 is secured or fastened to a distal end of the end effector 12. Alternately, dissecting tip 14 may be integrally formed with end effector 12 or end effector 12 and dissecting tip 14 may be of monolithic construction. Also, alternately dissecting tip 14 may be attached, or removably or releasably attached to end effector 12. In one preferred embodiment, dissecting tip 14 is secured to a distal surface of anvil assembly 34 which is contiguous or in direct or indirect communication with a tissue contact surface 34a of anvil assembly 34. Dissecting tip 14 may be formed from a surgical grade metal or plastic and attached to anvil assembly 34 using any known suitable fastening technique, e.g., adhesives, welding, soldering, brazing, pins, etc. Alternately, other known surgically approved materials may be used to construct dissecting tip 14. In this embodiment, dissecting tip 14 includes a curved smooth inner surface 14a, and also a curved, smooth outer surface 14b and a rounded thin blunt tip 14c. The curved surfaces can be formed having any suitable radius of curvature. A one inch radius has been found suitable for certain applications. Alternately, the curved surfaces may be formed having plural curved radii. The smooth surfaces prevent dissecting tip 14 from snagging, pulling and/or cutting tissue. Inner surface 14a of dissecting tip 14 extends downwardly towards cartridge assembly 36 to a location beyond the distal end of cartridge assembly 36. By extending dissecting tip 14 beyond cartridge assembly 36, access to adherent tissue is improved and visualization of the tip to confirm proper position and that dissection of the adherent tissue is completed is permitted. The width of dissecting tip 14 decreases from its proximal end to its distal end and at its greatest width is smaller than the width of cartridge assembly 36. Desirably there are substantially smooth blends or transitions from the dissecting tip to the portion(s) of the jaw structure to which the tip is secured or from which it extends. When anvil assembly 34 and cartridge assembly 36 are in the clamped or approximated position, dissecting tip 14 is spaced from a distal angled tissue guide surface 36a of cartridge assembly 36. In one embodiment, this space is at least the same, or greater, e.g., two times greater, than the gap between the tissue contacting surfaces of the anvil and cartridge assemblies when they are approximated. However, there may be instances when it may be desired to have less space between the dissecting tip and the tissue guide surface of the cartridge, for example when it is desired to compress tissue there.

Referring now to FIGS. 3-5, when surgical stapling device 10 is used to dissect certain tissue 40, e.g., blood or airway vessels, from target tissue 42, e.g., stomach, lung, etc., curved outer surface 14b of dissecting tip 14 can be pressed or passed against target tissue 42 and slid behind certain tissue 40, e.g., adherent, tissue to separate and/or dissect tissue 40 from, for example, adherence with target tissue 42. Positioning of dissecting tip 14 behind certain tissue 40 may be accomplished with anvil assembly 34 and cartridge assembly 36 in the open position. Alternately, the anvil and cartridge assemblies can be moved to the clamped position to provide extra stability to the end effector during dissection of tissue. Thereafter, either or both of certain tissue 40 and target tissue 42 can be independently joined and cut by clamping and actuating surgical stapling device 10.

It is noted that although not described in detail, end effector 12 may be adapted to access the surgical site through a trocar cannula assembly as is known in the art. To accomplish this, anvil assembly 34 and cartridge assembly 36 are maintained in a clamped position as elongated body portion 18 and end effector 12 are inserted through the cannula (not shown). As illustrated, dissecting tip 14 does not extend below a plane defined by a bottom surface 36b of cartridge assembly 36, nor does dissecting tip 14 extend outwardly beyond the sidewalls of cartridge assembly 36. The dissecting tip can be above, e.g., slightly above the plane. As such, surgical stapling device 10 including dissecting tip 14 may be used with a trocar cannula assembly sized to receive a surgical stapling device not having a dissecting tip 14.

FIGS. 6-6e illustrate another embodiment of the presently disclosed dissecting tip shown generally as 114. Dissecting tip 114 is secured to the distal end of end effector 12. Alternately, dissecting tip 114 may be monolithically or integrally formed with end effector 12. As discussed above, end effector 12 includes anvil assembly 34 and cartridge assembly 36. Dissecting tip 114 is secured to a distal surface or portion of anvil assembly 34 in the manner described above with respect to dissecting tip 14. Dissecting tip 114 is also constructed from a surgical grade metal or plastic and includes substantially flat inner and outer surfaces 114a and 114b and a rounded, blunt tip 114c. The use of other known surgically approved materials to construct dissecting tip 114 is envisioned. Other tip configurations may be employed. The outer edges 114d of outer surface 114b may be rounded to prevent snagging, and/or cutting of tissue. Inner surface 114a of dissecting tip 114 is substantially parallel to and spaced from tissue guide surface 36a of cartridge assembly 36 when anvil assembly 34 and cartridge assembly 36 are in the clamped position. Distal tip 114c of dissecting tip 114 extends distally beyond the distal end of cartridge assembly 36 and decreases in width from its proximal end to its distal end. The width of the proximal end of dissecting tip 114 is smaller than the width of cartridge assembly 36 and distal tip 114c does not extend below a plane defined by a bottom surface 36b of cartridge assembly 36. As such, a surgical stapling device including dissecting tip 114 can be inserted through a trocar cannula assembly sized to receive the stapling device.

The use of dissecting tip 114 is substantially identical to that of dissecting tip 14 and will not be discussed in further detail herein.

Figure 7:
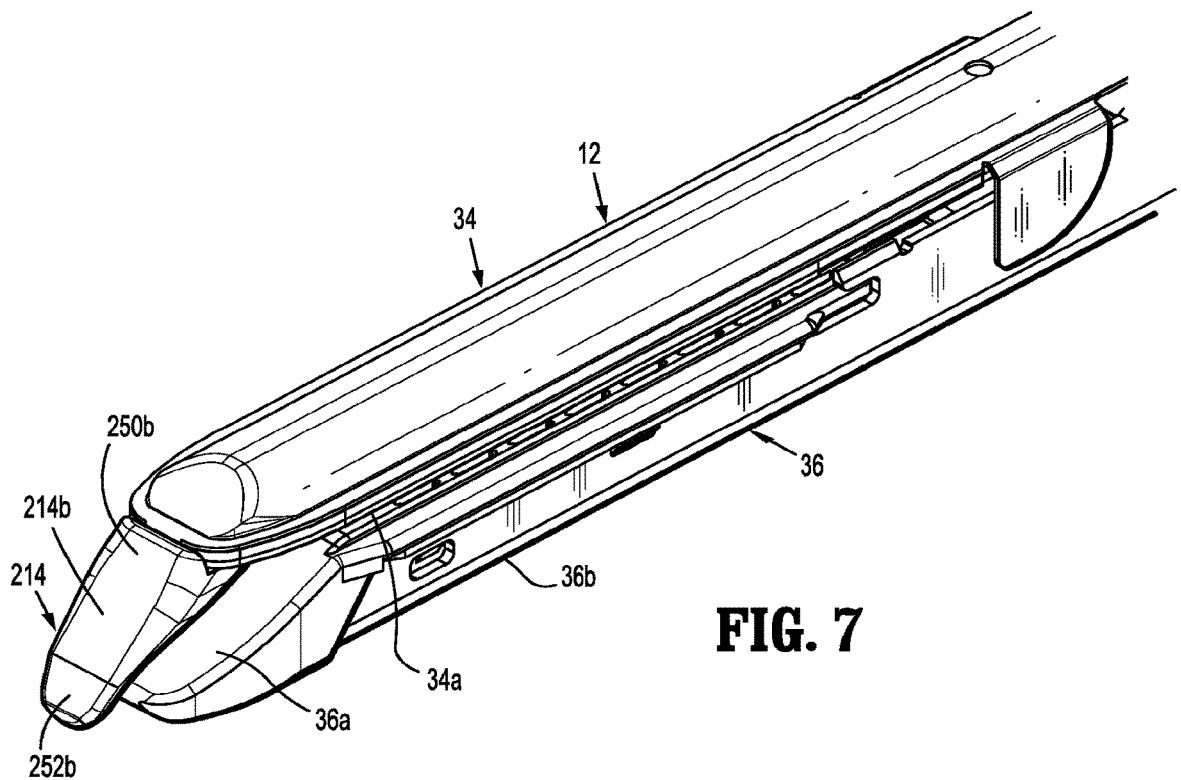
FIG. 7 is an enlarged side top perspective view from the front of the end effector of a surgical stapling device including another embodiment of the presently disclosed dissecting tip.

FIGS. 7-7e illustrate yet another embodiment of the presently disclosed dissecting tip shown generally as 214. Dissecting tip 214 is secured to anvil assembly 34 of end effector 12 in the manner described above with respect to dissecting tip 14. Dissecting tip 214 is also constructed from a surgical grade metal or plastic. Alternatively, the use of other known materials of construction is envisioned.

Figure 7A:
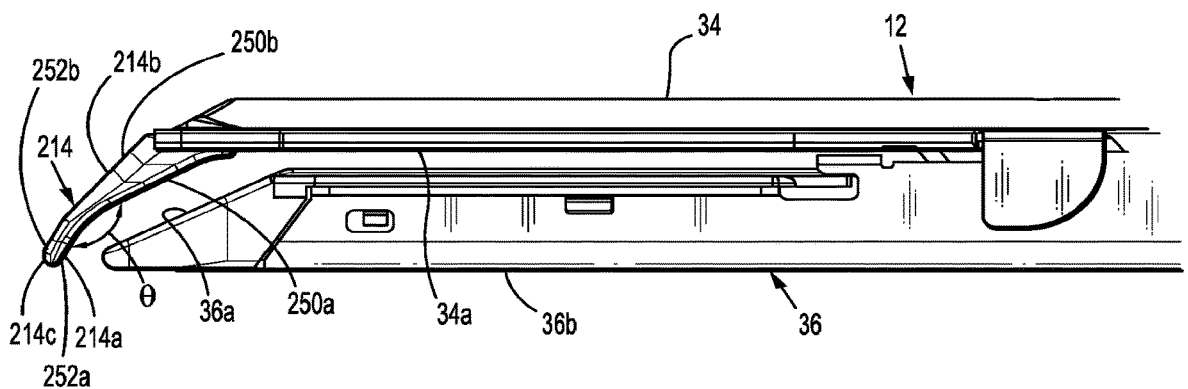
FIG. 7a is a side view of the dissecting tip and end effector shown in FIG. 7.

Dissecting tip 214 includes inner and outer surfaces 214a and 214b and a blunt tip 214c. Inner and outer surfaces 214a and 214b each have a substantially flat proximal portion 250a and 250b and a substantially flat distal portion 252a and 252b positioned at an angle to proximal portion 250. In one embodiment, proximal portion 250 and distal portion 252, along inner surface 214a, define an angle.THETA. (FIG. 7a) of between about 90.degree. and about 170.degree. In one embodiment, angle.THETA. is about 30.degree. The transition between proximal portion 250a and distal portion 252a is smooth and rounded to prevent snagging, pulling and/or cutting of tissue. The outer surface of tip 214 can have other shapes, e.g., rounded as in FIGS. 1-5e. As discussed above with respect to dissecting tips 14 and 114, the width of dissecting tip 214 decreases from its proximal end to its distal end and at its greatest width is less than the width of cartridge assembly 36. The distal end of distal portion 252a includes a blunt tip 214c which in this embodiment does not extend beyond a plane defined by a bottom surface 36b of cartridge assembly 36. The use of dissecting tip 214 is substantially identical to that of dissecting tip 14 and will not be discussed in further detail herein.

Figure 8:
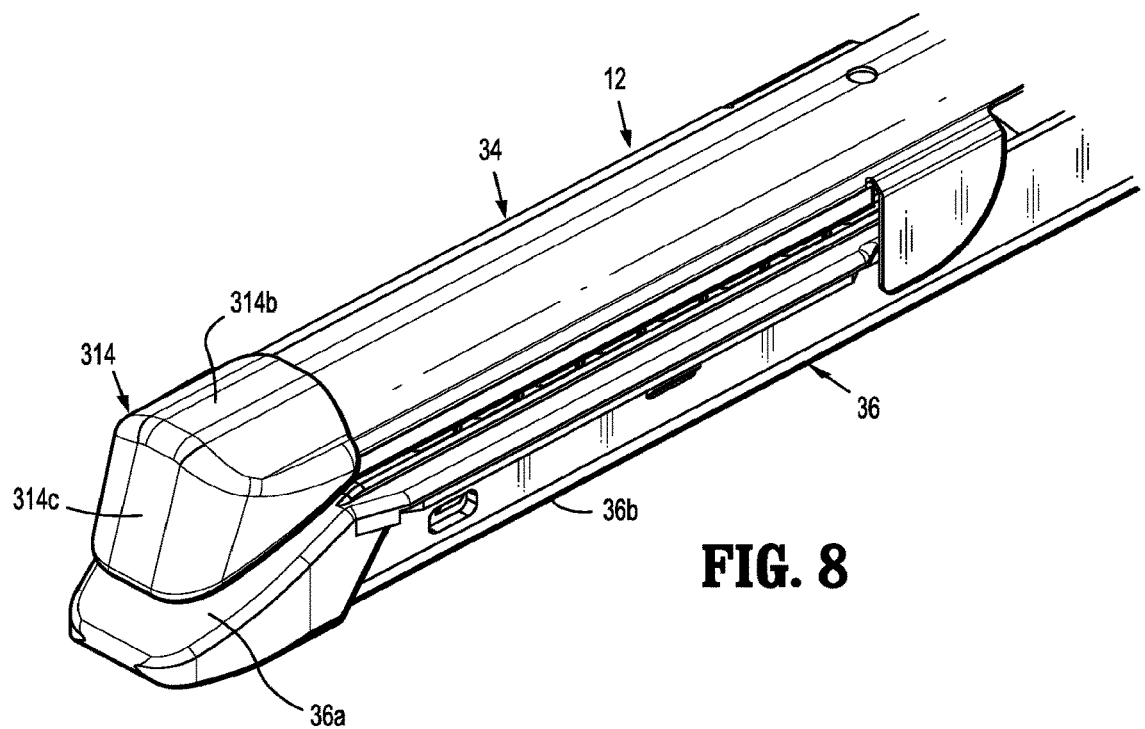
FIG. 8 is an enlarged side perspective view from the front of the end effector of a surgical stapling device including yet another embodiment of the presently disclosed dissecting tip.
Figure 8A:
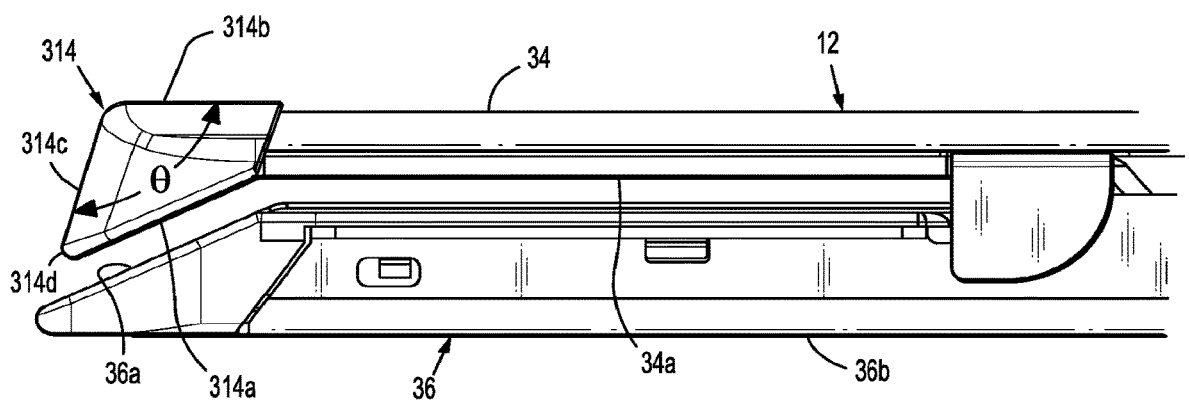
FIG. 8a is a side view of the dissecting tip and end effector shown in FIG. 8.

FIGS. 8-8e illustrate another embodiment of the presently disclosed dissecting tip shown generally as 314. Dissecting tip 314 includes an inner surface 314a, a top surface 314b and a front surface 314c. Inner surface 314a is angled and is substantially parallel to distal angled tissue guide surface 36a of cartridge assembly 36. Top surface 314b is curved or concave along an axis transverse to a longitudinal axis of anvil assembly 34. Front surface 314c is angled downwardly towards cartridge assembly 36 and defines an angle.THETA. (FIG. 8a) of between about 95.degree. and 135.degree. with respect to the longitudinal axis of anvil assembly 34. In one embodiment, angle.THETA. is about 106.degree. The width of dissecting tip 314 decreases from a proximal end of dissecting tip 314 to the distal end of dissecting tip 314. The width at the proximal end of dissecting tip 314 is approximately equal to the width of cartridge assembly 36. As discussed above, the dimensions and positioning of dissecting tip 314 on stapling device 10 permit positioning of stapling device 10 through a trocar cannula assembly sized to allow passage stapling device 10 without dissecting tip 314.

Distal tip 314d of dissecting tip 314 may be positioned proximally of the distal end of cartridge assembly 36. Alternately, distal tip 314d may be positioned adjacent to or distally of the distal end of cartridge assembly 36.

Dissecting tip 314 includes a substantially hollow recess 314e (FIG. 8f) which is configured to receive the distal end of anvil assembly 34. Dissecting tip 314 may be positioned over the distal end of anvil assembly 34 and secured thereto using any known fastening technique, e.g., adhesives, welding, friction fit, pins, screws, etc. Dissecting tip 314 may be formed from surgical grade metals or plastics although other known materials of construction are envisioned. Dissecting tip 314 functions basically in the same manner as discussed above with respect to dissecting tip 14 and will not be discussed in further detail herein.

Figure 9:
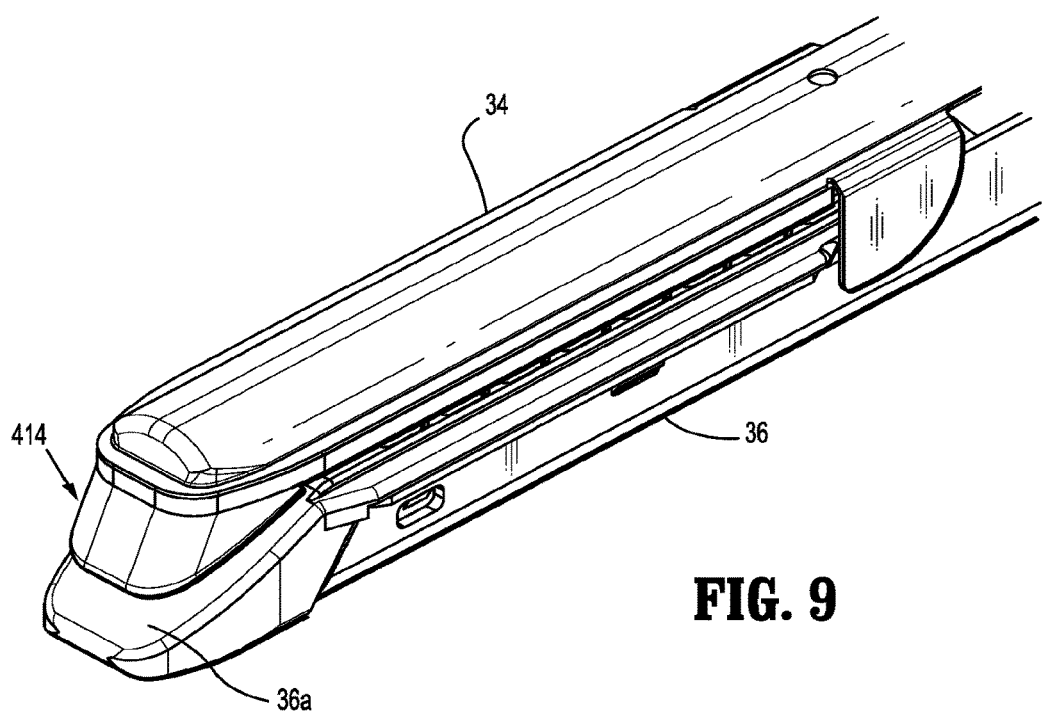
FIG. 9 is an enlarged top side perspective view from the front of the end effector of a surgical stapling device including another preferred embodiment of the presently disclosed dissecting tip.
Figure 9A:
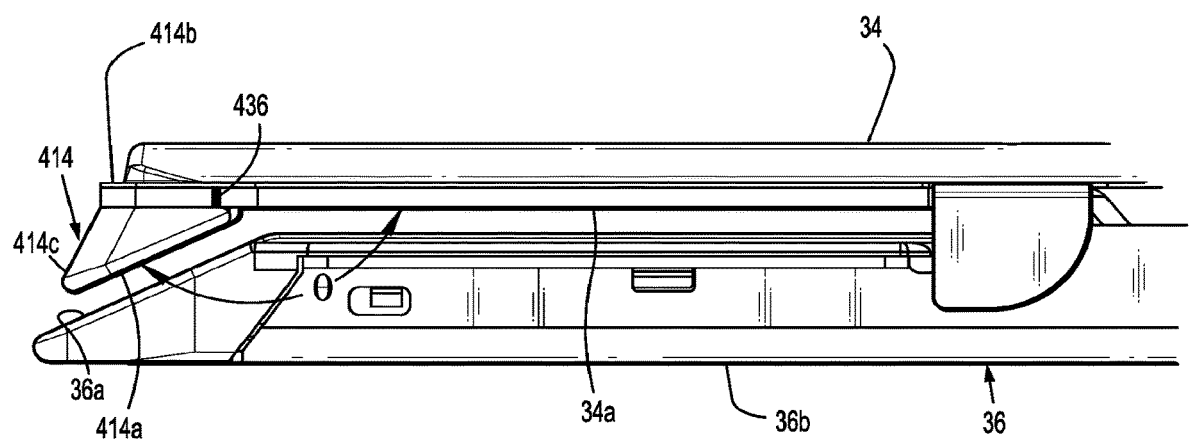
FIG. 9a is a side view of the dissecting tip and end effector shown in FIG. 9.

FIGS. 9-9e illustrate yet another embodiment of the presently disclosed dissecting tip shown generally as 414. Dissecting tip 414 is similar in shape to dissecting tip 314 but includes a peg extension 436 (FIG. 9e) to secure dissecting tip 414 to anvil assembly 34, rather than a hollow recess as will be further discussed below. Dissecting tip 414 includes an inner surface 414a, a top surface 414b, and a front surface 414c. Inner surface 414a is substantially parallel to a tissue guide surface 36b on the distal end of cartridge assembly 36. Top surface 414b is flat and is positioned to abut against a distal surface of anvil assembly 34 which is contiguous with an inner tissue engaging surface 34a of anvil assembly 34. Front surface 414c is angled downwardly towards cartridge assembly 36 and in one embodiment defines an angle .THETA. (FIG. 9a) of between about 95.degree. and about 135. In one embodiment, angle .THETA. is about 154.degree.

Peg extension 436 is a T-shaped member which extends upwardly from a proximal end of top surface 414b of dissecting tip 414. The upper portion 452 of T-shaped member 436 extends transversely across anvil assembly 34 and is dimensioned to be received in a linear slot (not shown) formed in the distal end of anvil assembly 34. To attach dissecting tip 414 to anvil assembly 34, upper portion 452 of T-shaped member 436 is positioned within the distal linear slots of anvil assembly 34 and dissecting tip 414 is rotated 90.degree. to lock upper portion 452 within the linear slot and lock dissecting tip to anvil assembly 34. Additional fastening techniques may be used to fixedly secure dissecting tip 414 to anvil assembly 34, e.g., adhesives, welding, etc.

Figure 10:
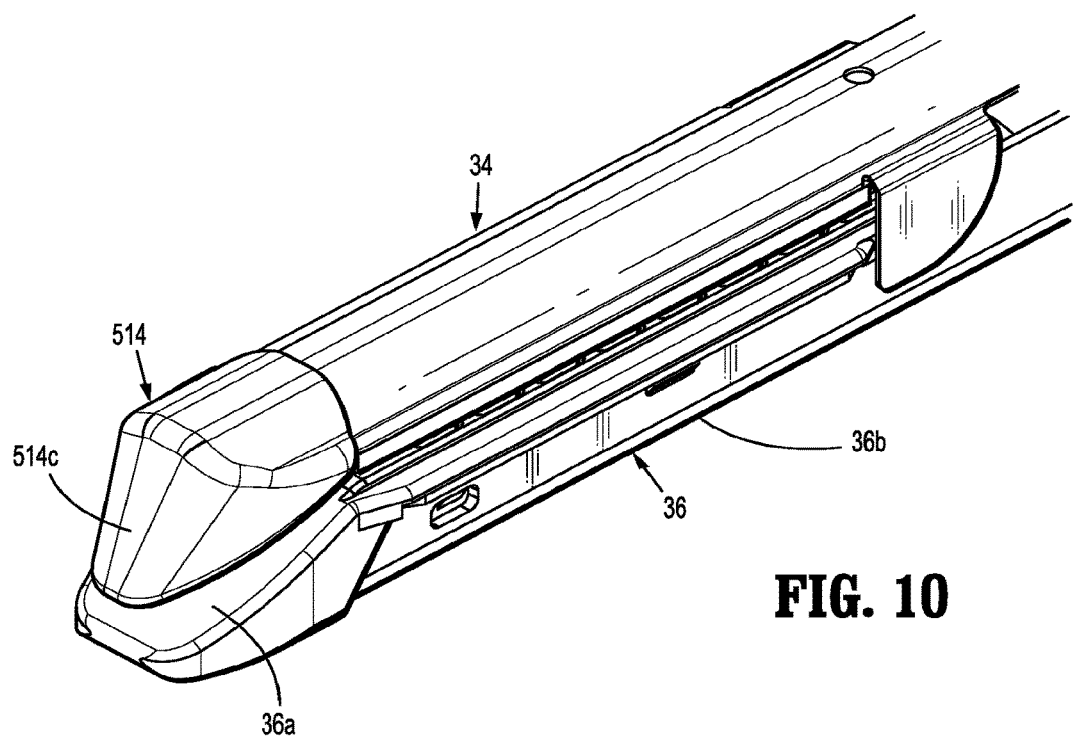
FIG. 10 is an enlarged side perspective view from the front of the end effector of a surgical stapling device including another embodiment of the presently disclosed dissecting tip.
Figure 10A:
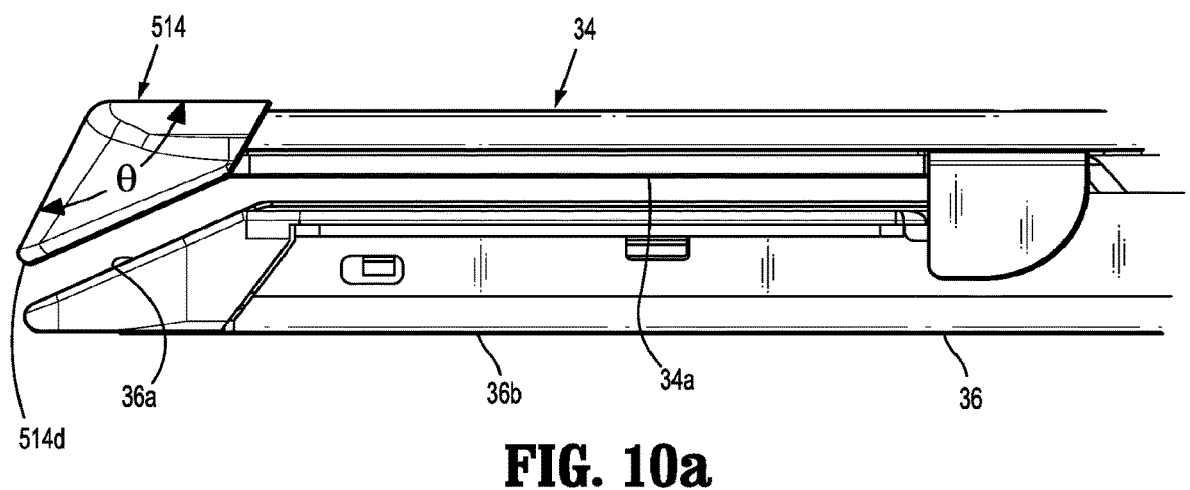
FIG. 10a is a side view of the dissecting tip and end effector shown in FIG. 10.
Figure 10B:
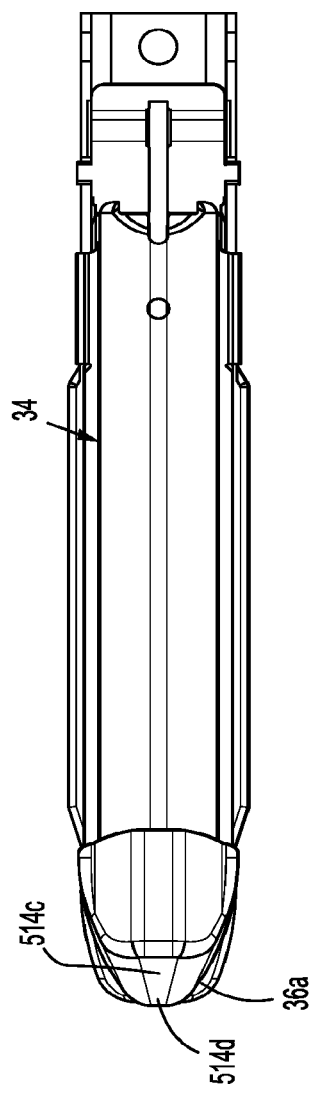
FIG. 10b is a top view of the dissecting tip and end effector of the surgical stapling device shown in FIG. 10.
Figure 10C:
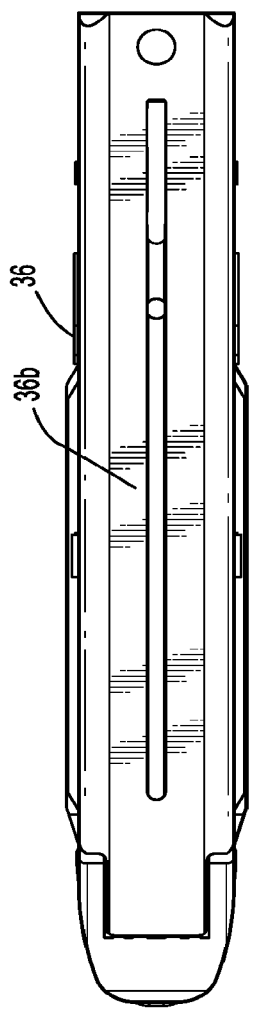
FIG. 10c is a bottom view of the dissecting tip and end effector shown in FIG. 10b.
Figure 10E:
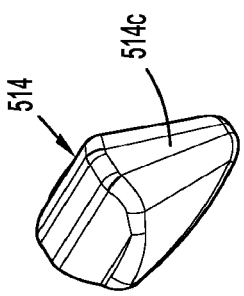
FIG. 10e is a side perspective view from the front of the presently disclosed dissecting tip shown in FIG. 9.
Figure 10D:
FIG. 10d is a front view of the dissecting tip and end effector shown in FIG. 10c.

FIGS. 10-10e illustrate another embodiment of the presently disclosed dissecting tip shown generally as 514. Dissecting tip 514 is substantially similar to dissecting tip 314 in construction but differs in that a distal tip 514d of dissecting tip 514 is narrower than and positioned above, over or adjacent to the distal end of cartridge assembly 36. Further, top surface 514b and front surface 514c together define an angle.THETA. (FIG. 10a) of between about 95.degree. and about 135.degree. In one embodiment, angle-.THETA. is about 115.degree. As discussed above with respect to dissecting tip 314, dissecting tip 514 defines a hollow recess (not shown) dimensioned and configured to receive the distal end of anvil assembly 34.

Figure 11:
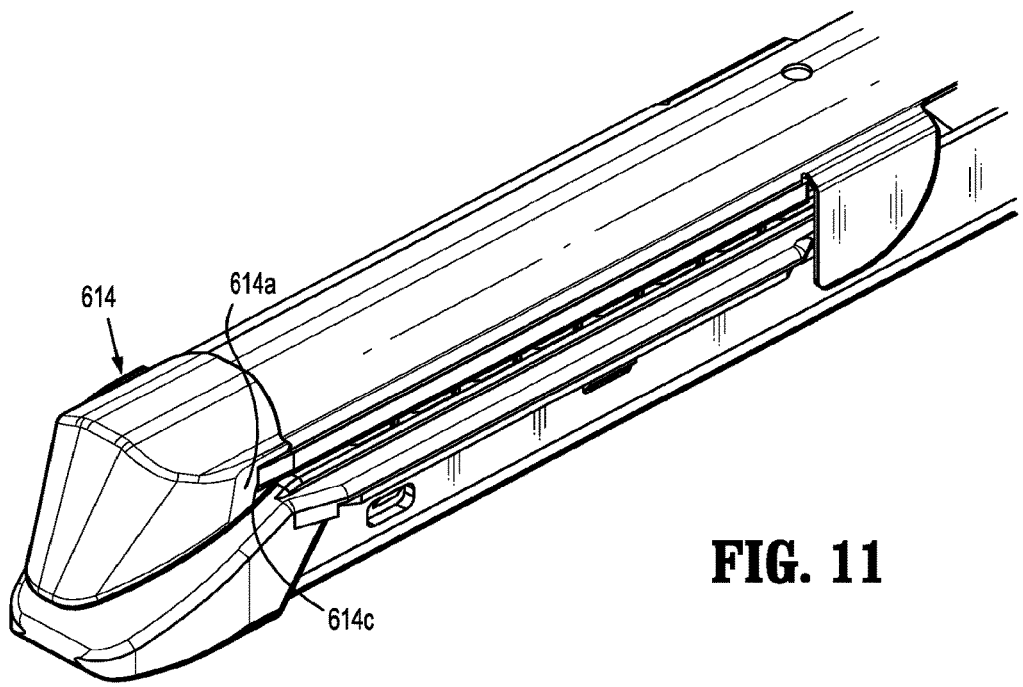
FIG. 11 is an enlarged side perspective view from the front of the end effector of a surgical stapling device including another embodiment of the presently disclosed dissecting tip.
Figure 11A:
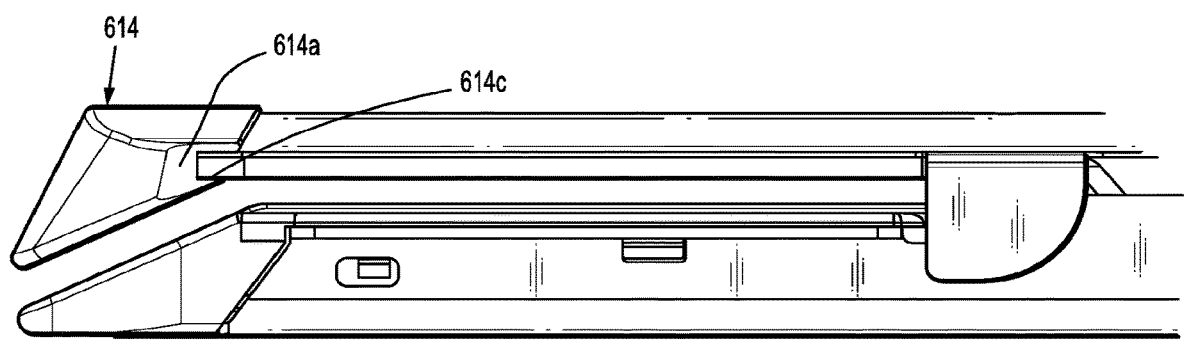
FIG. 11a is a side view of the dissecting tip and end effector shown in FIG. 11.

FIGS. 11-11e illustrate yet another embodiment of the presently disclosed dissecting tip shown generally as 614. Dissecting tip 614 is substantially similar to dissecting tip 514 with the exception that dissecting tip 614 includes a pair of cutouts 614c formed in opposite tapered sidewalls 614a and 614b thereof. The tapered sidewalls 614a and 614b and cutouts 614c provide a smooth transition from dissecting tip 614 to anvil assembly 34 to prevent snagging and pulling of tissue.

Figure 12:
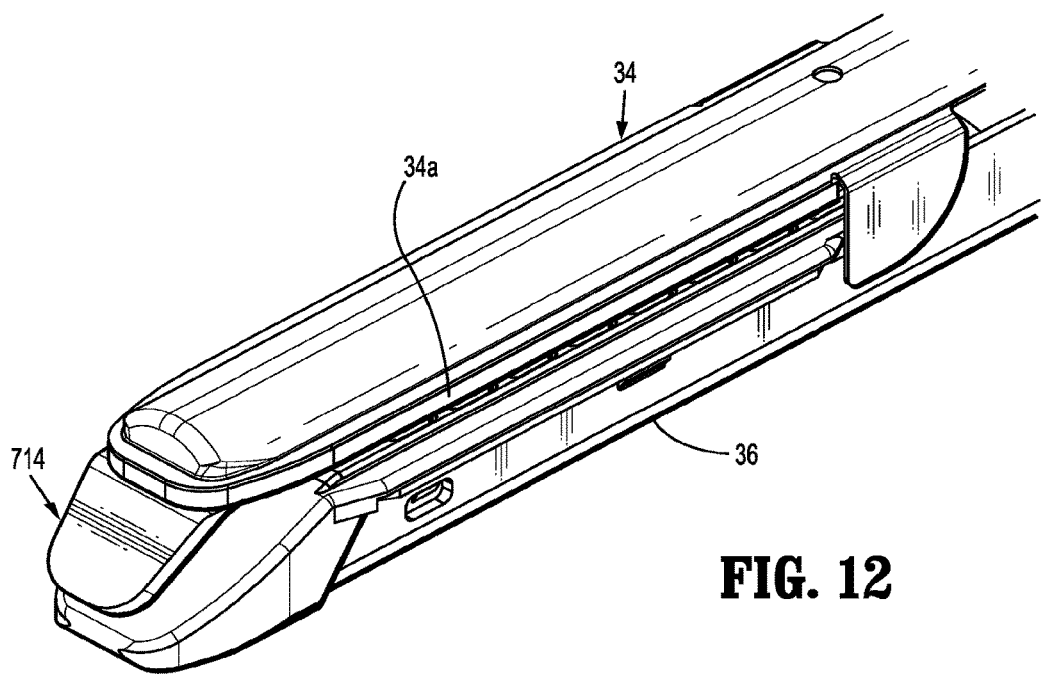
FIG. 12 is an enlarged side top perspective view from the front of the end effector of a surgical stapling device including another embodiment of the presently disclosed dissecting tip.

FIG. 12-12e illustrate another embodiment of the presently disclosed dissecting tip shown generally as 714. Dissecting tip 714 is formed integrally and/or monolithically with an anvil plate 34a (FIG. 12e) of anvil assembly 34 and is therefore formed from a surgical grade metal. Dissecting tip 714 includes an inner surface 714a, an outer surface 714b and a distal tip 714c which may be rounded. Inner and outer surfaces 714a and 714b are substantially flat and define an angle.THETA. of between about 105.degree. and about 155.degree. in relation to a longitudinal axis of anvil assembly 34. In one embodiment, .THETA. is about 136.degree. Dissecting tip 714 extends downwardly towards cartridge assembly 36, at angle.THETA. which in one embodiment is less than an angle B defined between tissue guide surface 36a formed on the distal end of cartridge assembly 36 and a longitudinal axis of cartridge assembly 36. Although the dissecting tip of this disclosure can be employed on any sized SULU or end effector, for some applications shorter end effectors may be preferred.

Figure 12A:
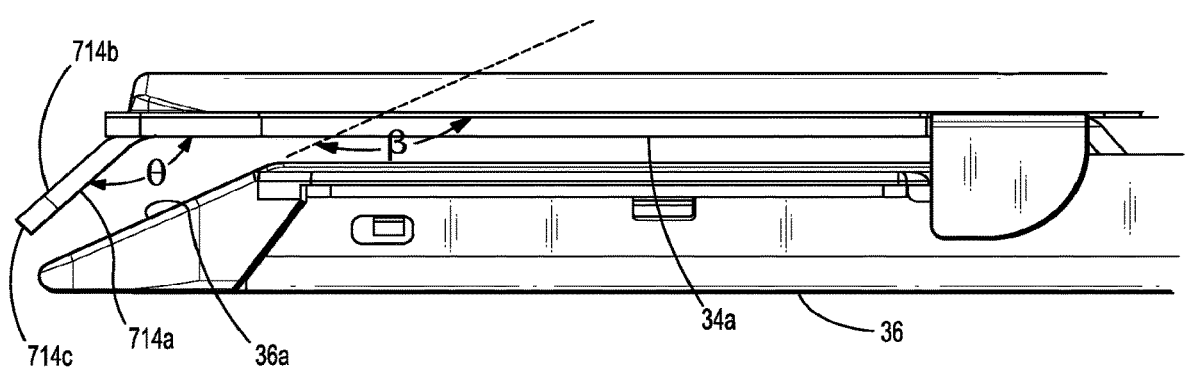
FIG. 12a is a side view of the dissecting tip and end effector shown in FIG. 12.

The junction, blend or transition of the proximal portion of the inner surface of dissecting tip 14 with the plane of tissue contacting surface 34 of the anvil assembly may be positioned axially distal of the junction, blend or transition of tissue guide surface 36a and the tissue contacting surface of cartridge assembly 36. This provides space to allow tissue to be squeezed distally of the staple working portions of the tissue contacting surfaces of anvil assembly 34 and cartridge assembly 36 and helps maintain the desired tissue gap between those surfaces, during approximation and clamping. The configuration of dissecting tip 714 of end effector 12 shown in FIG. 12a exemplifies this junctional relationship.

Figure 13:
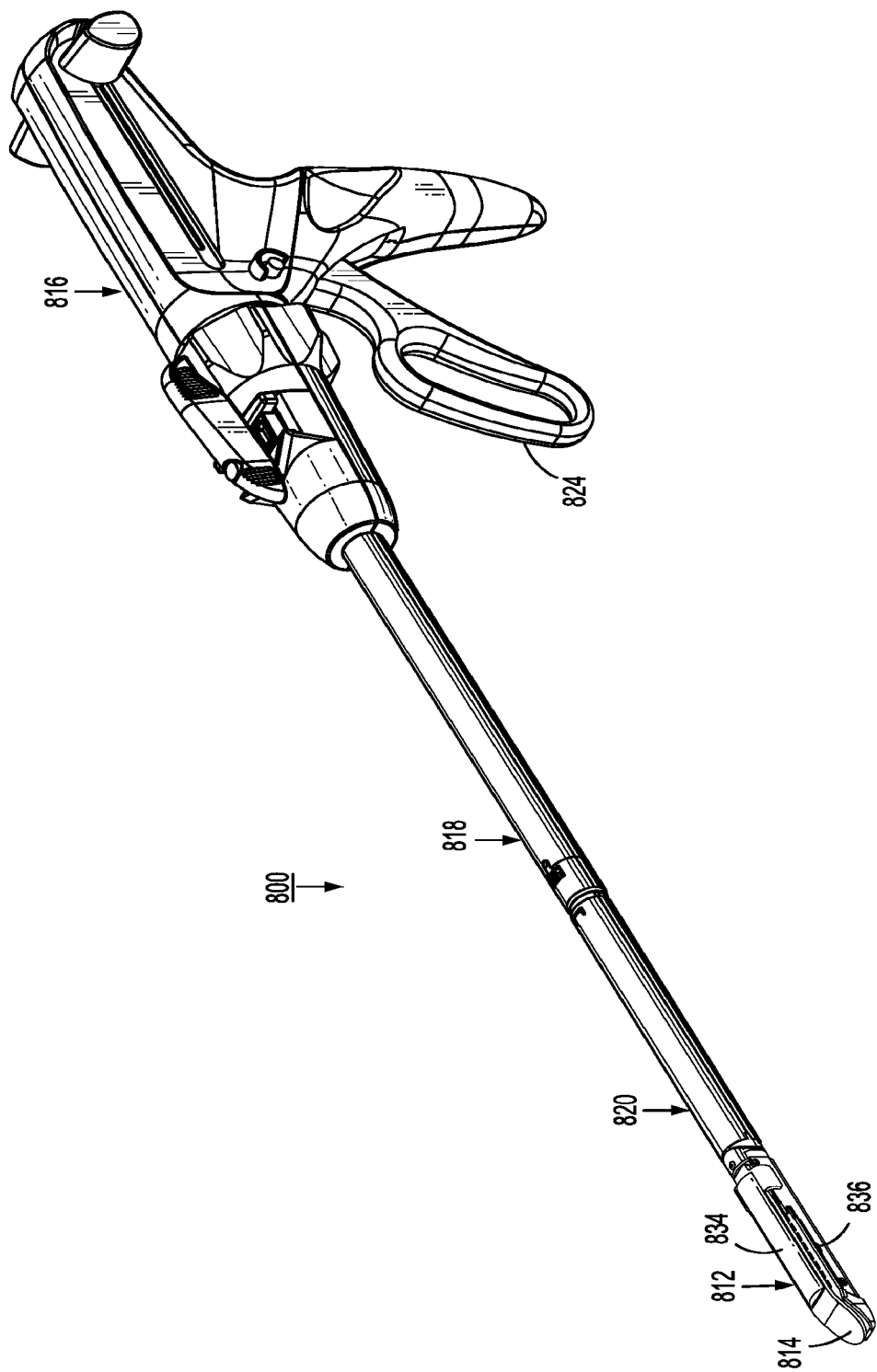
FIG. 13 is a side perspective view from above a surgical stapling device including another embodiment of the presently disclosed dissecting tip attached to the end effector thereof with the anvil assembly and cartridge assembly of the end effector in the closed or clamped position.
Figure 13A:
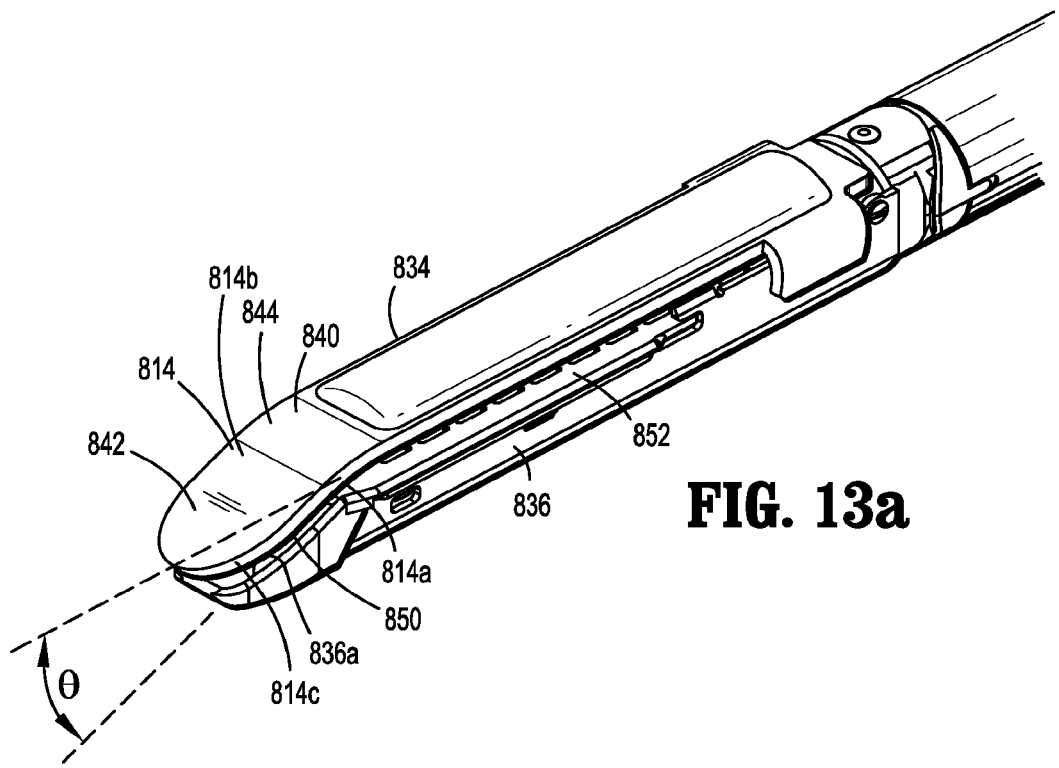
FIG. 13a is an enlarged side perspective view from above of the end effector of the surgical stapling device shown in FIG. 1 with the anvil assembly and cartridge assembly in the clamped position.
Figure 13B:
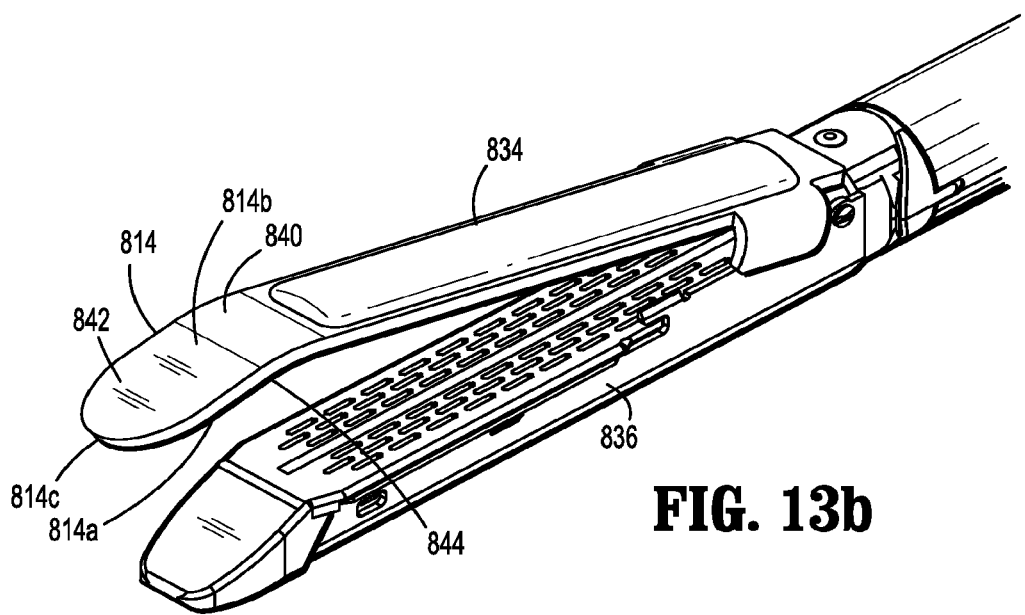
FIG. 13b is an enlarged side perspective view from above of the end effector of the surgical stapling device shown in FIG. 1 with the anvil assembly and cartridge assembly in the open position.
Figure 14A:
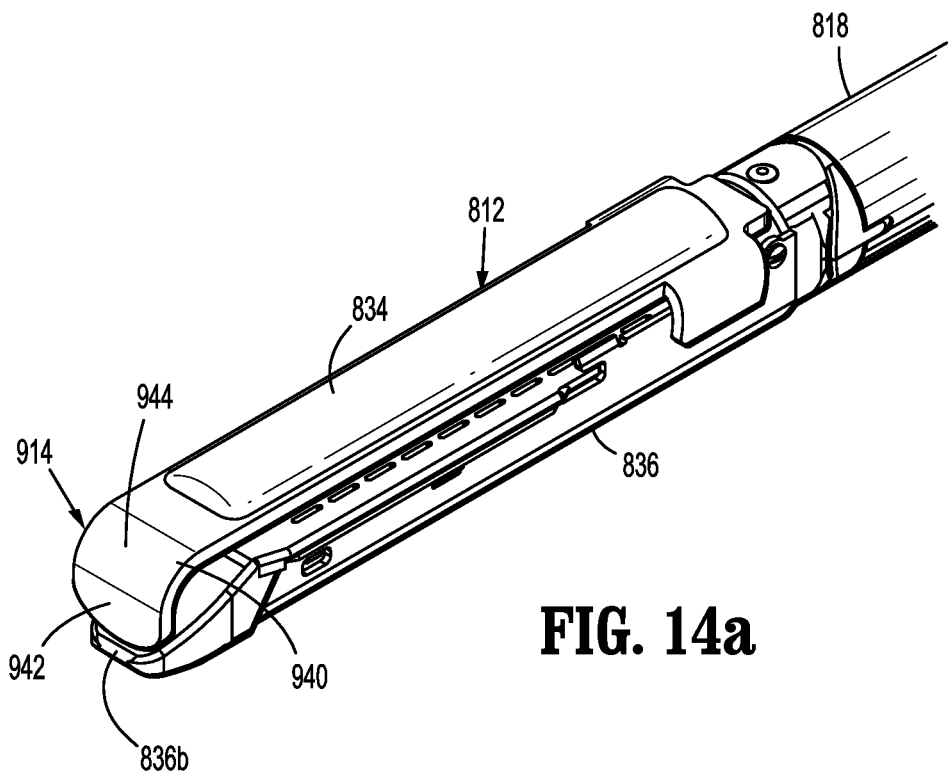
FIG. 14a is an enlarged side perspective view from above of another embodiment of the presently disclosed dissecting tip attached to an end effector with the anvil assembly and cartridge assembly of the end effector in the closed or clamped position.
Figure 14B:
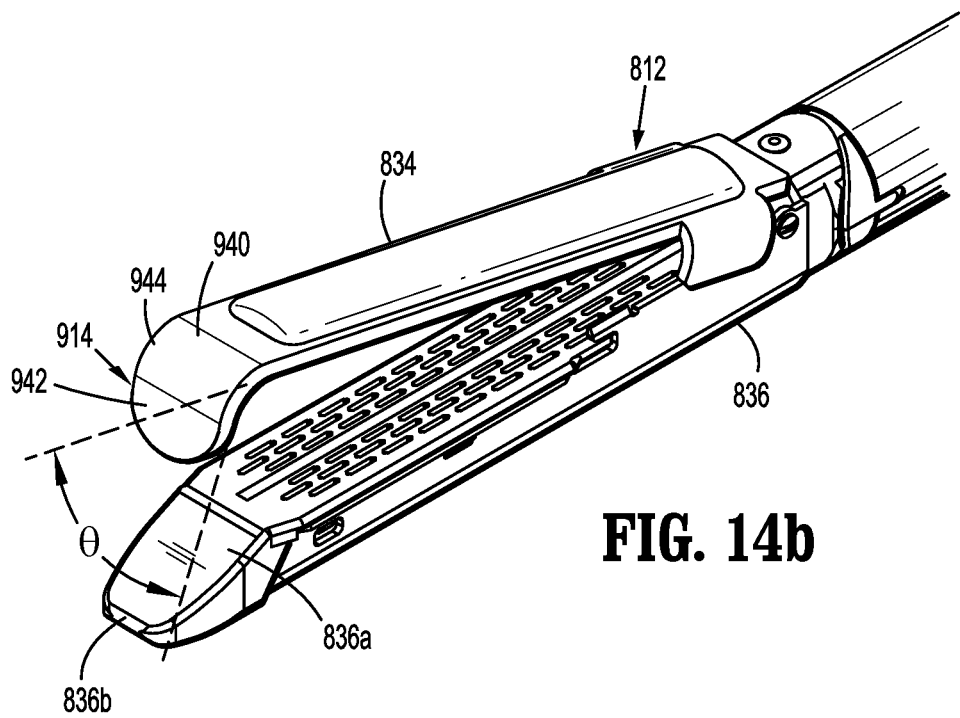
FIG. 14b is a side perspective view from above of the presently disclosed dissecting tip and end effector shown in FIG. 14a with the anvil assembly and cartridge assembly of the end effector in the open position.

FIG. 13 illustrates a linear surgical stapling device shown generally as 800 including an end effector 812 having another embodiment of the presently disclosed dissecting tip here designated 814, supported thereon. Stapling device 800 is substantially similar to stapling device 10 and includes a handle assembly 816 and an endoscopic portion 818. End effector 812 may form part of a disposable loading unit or single use loading unit (SULU) 820.

Referring to FIGS. 13a-13f, end effector 812 includes an anvil assembly 834 and a cartridge assembly 836 movably positioned (pivotally or otherwise) in relation to each other between an open position (FIG. 13b) and a clamped or approximated position (13a). In one embodiment, anvil assembly 834 is pivotal in relation to cartridge assembly 836. Trigger 824 is movable through an actuation stroke or strokes to move anvil assembly 834 and cartridge assembly 836 between the open and closed positions as is well known in the art.

Referring to FIGS. 13a-13f, dissecting tip 814 extends distally from end effector 812. In this embodiment, dissecting tip 814 and anvil assembly 834 are of monolithic construction. Alternately, it is envisioned that dissecting tip 814 may be formed separately from anvil assembly 834 and secured thereto using any known fastening technique, e.g., adhesives, welding, soldering, brazing, pins, interlocking structure, etc. It is envisioned that the dissection tips of the embodiments disclosed herein can be selectively removable and replaceable. It is contemplated that dissecting tip 814 can be supported on another portion of end effector 812 such as cartridge assembly 836. Dissecting tip 814 may be formed from a surgical grade metal or plastic. It is also contemplated, however, that other known surgically approved materials may be used to construct dissecting tip 814.

Dissecting tip 814 includes a proximal portion 840 and a distal portion 842. Proximal portion 840 extends distally from anvil assembly 834 and includes a curved section 844. Curved section 844 defines a smooth transition between anvil assembly 834 and distal portion 842 of dissecting tip 814. The longitudinal axis of anvil assembly 834 and the longitudinal axis of distal portion 842 of dissecting tip 814 intersect to define any suitable angle .THETA. (FIG. 13a) between about 5.degree. and about 90.degree. In this embodiment angle .THETA. is about 30.degree.

Distal portion 842 includes a semi-circular smooth distal face 814c. Proximal portion 840 and distal portion 842, together, define a smooth substantially flat inner surface 814a and a smooth substantially flat outer surface 814b. As illustrated, the width of dissecting tip 814 proximal of distal face 814c is substantially constant along the length of dissecting tip 814 and is about equal to the width of anvil assembly 834. The width of dissecting tip 814a can also be about equal to the width of cartridge assembly 836. It is contemplated, however, that the width of dissecting tip 814 may be any suitable width and may vary along the length of dissecting tip, e.g., the width of dissecting tip 814 may be decreased or increased along the length of dissecting tip 814 from the proximal end of dissecting tip 814 to the distal end of the dissecting tip 814 or at any point therebetween. In this embodiment, the width of dissecting tip 814 does not exceed the width of cartridge assembly 836. This embodiment is suitable for insertion through standard trocars and lumens for laparoscopic or endoscopic procedures.

As illustrated in FIGS. 13a and 13c-13f, when anvil assembly 834 and cartridge assembly 836 are in their clamped position, a gap 850 is defined between a distal angled guide surface 836a of cartridge assembly 836 and inner surface 814a of dissecting tip 814. In this embodiment, gap 850 is substantially equal to or greater that gap 852 defined between the anvil and cartridge assemblies. It is envisioned that in some circumstances it may be desirable to reduce the height of gap 850 to a height smaller than gap 852, e.g., when it is desirable to clamp or compress tissue between guide surface 836a of cartridge assembly 836 and inner surface 814a of dissecting tip 814.

FIGS. 14a-14f illustrate another embodiment of the presently disclosed dissecting tip shown generally as 914. Dissecting tip 914 extends distally from end effector 812. In one embodiment, dissecting tip 914 is formed monolithically with anvil assembly 834 of end effector 812. Alternately, it is envisioned that dissecting tip 914 may be formed separately from anvil assembly 834 and secured thereto using any known fastening technique as set forth above. It is also envisioned that dissecting tip 914 can be supported by another portion of end effector 812 such as cartridge assembly 836. Dissecting tip 914 may be formed from surgical grade metals or plastics having the requisite strength requirements or any other known material suitable for surgical use.

Dissecting tip 914 is substantially similar in shape to dissecting tip 814 with the exception that angle .THETA. is about 90.degree. and that there is a reduced radius of curvature leading distally to downturned distal portion 942 of dissector tip 914. More specifically, dissecting tip 914 includes a proximal portion 940 and a distal portion 942. Proximal portion 940 extends distally from anvil assembly 834 and includes a curved section 944 which defines a smooth transition between anvil assembly 834 and distal portion 942 of dissecting tip 914. The longitudinal axis of anvil assembly 834 and the longitudinal axis of distal portion 942 of dissecting tip 914 define an angle .THETA. of between about 80.degree. and about 90.degree.

Figure 15:
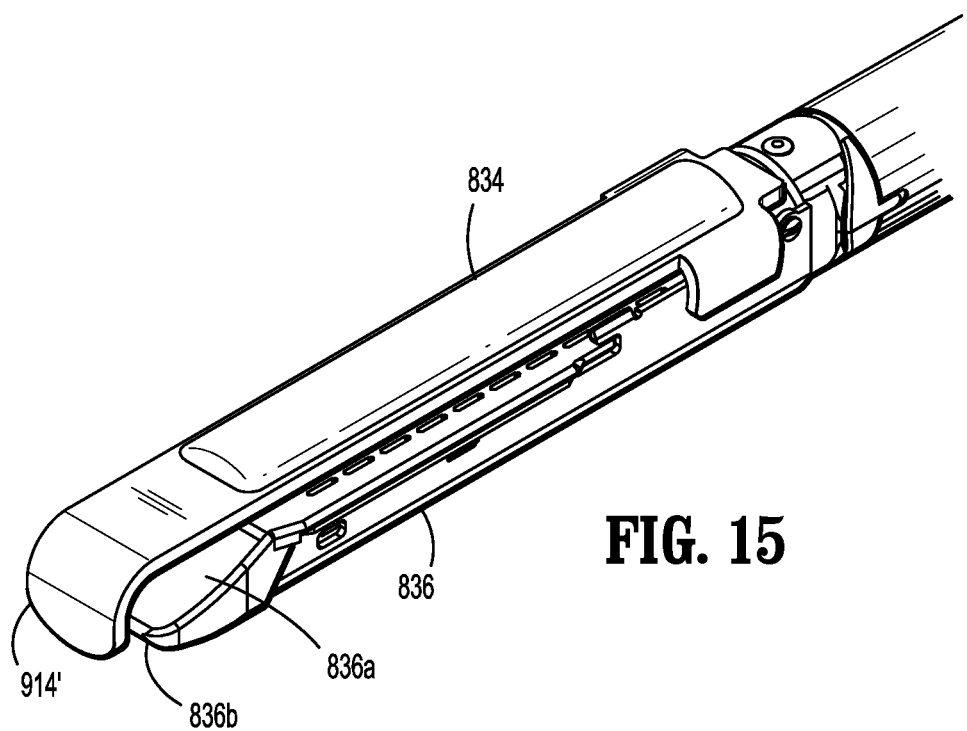
FIG. 15 is a side perspective view from above of another embodiment of the presently disclosed dissecting tip attached to an end effector with the anvil assembly and cartridge assembly of the end effector in the closed or clamped position.
Figure 15A:
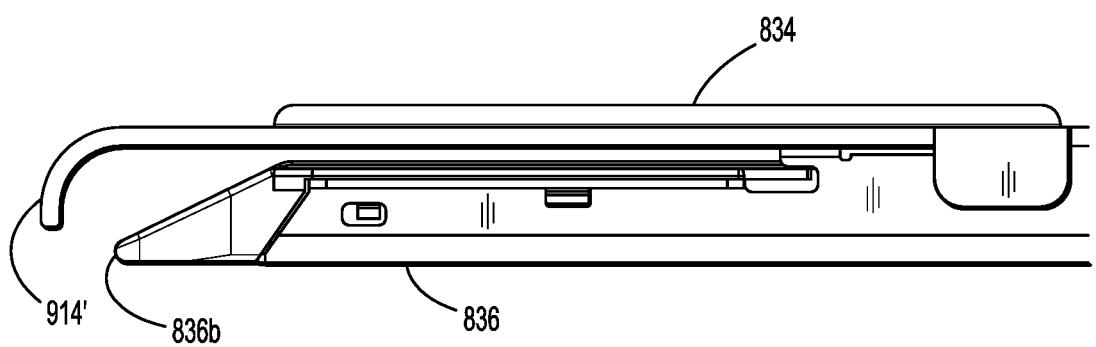
FIG. 15a is a side view of the end effector and dissecting tip shown in FIG. 15.

Distal portion 942 is similar in shape to that of distal portion 842 of dissecting tip 814 and will not be discussed in further detail here. In one embodiment (See FIGS. 14a-14f), distal portion 942 of dissecting tip 914 extends distally to about or adjacent the distal end 836b of cartridge assembly 836 of end effector 812. In another embodiment (See FIGS. 15 and 15a), dissecting tip 914' is positioned distally of the distal end 836b of cartridge assembly 836 of end effector 812. In this embodiment, dissecting tip 914' is positioned to dissect tissue when the anvil and cartridge assemblies are in their clamped position and to reach further ahead of the end effector, e.g., the cartridge distal guide surface, to facilitate passage between or behind tissue and facilitate isolation and positioning of larger tissue with the jaws of end effector 912.

Figure 16A:
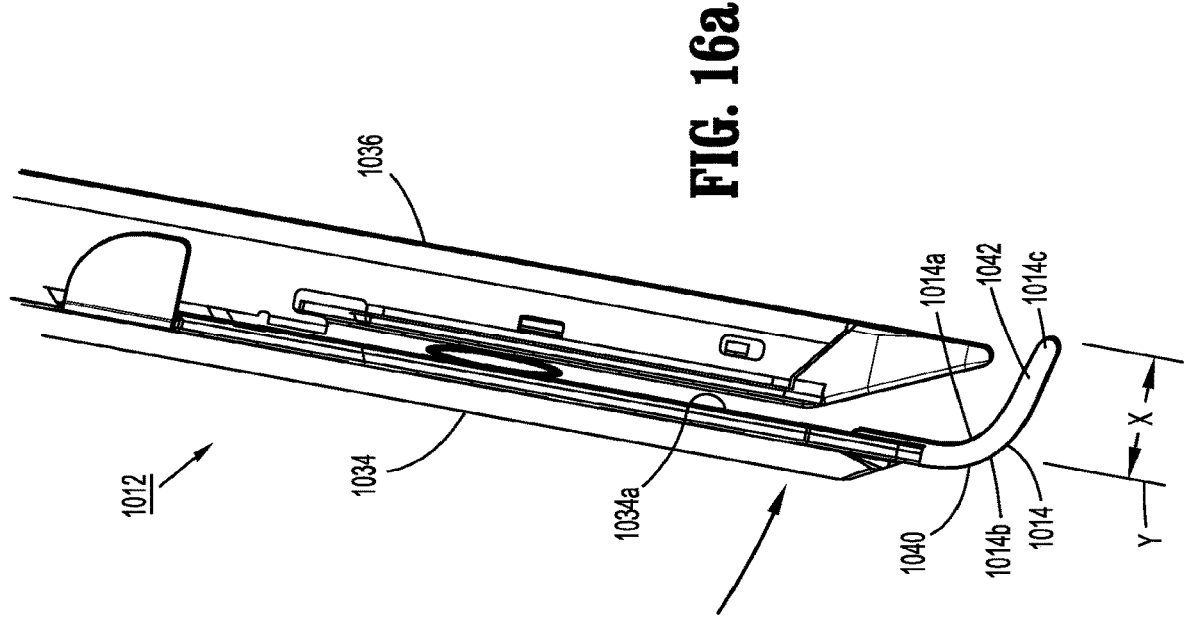
FIG. 16a is a side view of the end effector and dissecting tip shown in FIG. 16 with the anvil assembly and cartridge assembly of the end effector in the clamped position.
Figure 16:
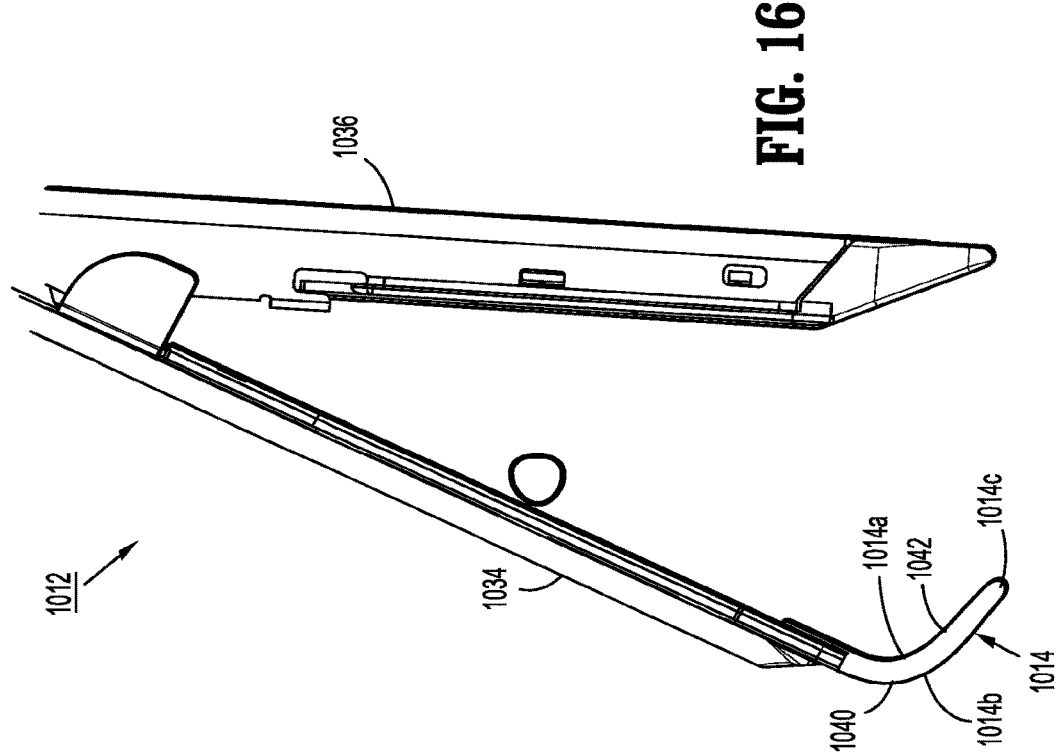
FIG. 16 is a side view of another embodiment of the presently disclosed dissecting tip attached to an end effector of a surgical instrument with the anvil assembly and the cartridge assembly of the end effector in an open position.

FIGS. 16-16e illustrate another embodiment of the presently disclosed dissecting tip shown generally as 1014. Dissecting tip 1014 is secured to the distal end of anvil assembly 1034 of end effector 1012 using any known suitable fastening technique, e.g., adhesives, welding, soldering, brazing, pins, etc. It is also envisioned that dissecting tip 1014 may be secured to end effector 1012 at other locations such as to cartridge assembly 1036. Alternately, dissecting tip 1014 may be formed monolithically or integrally with or removably attached to a portion of end effector 1012. Dissecting tip 1014 may be constructed from a surgical grade metal or plastic, although it is contemplated that other surgically approved materials may be used.

Dissecting tip 1014 includes a proximal portion 1040 and a distal portion 1042. Proximal and distal portions 1040 and 1042, respectively, are contiguous and define a curved inner surface 1014a, a corresponding curved outer surface 1014b and a distal tip 1014c. Distal tip 1014c is located on the distal end of distal portion 1042. In one embodiment, surfaces 1014a and 1014b are smooth to prevent dissecting tip 1014 from snagging, pulling and/or cutting tissue. In one embodiment, the width of distal portion 1042 of dissecting tip 1014 decreases substantially continuously from its proximal end 1040 to its distal end 1042 and culminates at distal tip 1014c which may be thin and blunt or rounded (See FIGS. 16d and 16e). It is also contemplated, however, that the width of the distal portion and/or proximal portion of dissecting tip 1014 may remain constant along its length or have a width which increases or decreases along any portion or all of its length. As understood throughout this disclosure, the width of dissecting tip 1014 at its greatest point should be less than the width of cartridge assembly 1036 to facilitate insertion of end effector 1012 through a trocar assembly during endoscopic procedures. Alternately, where dissecting tip 1014 is employed on open surgical instruments, it may be desirable to increase the width of dissector tip 1014 beyond that of cartridge assembly 1036. Such would increase visibility of the tip to the surgeon.

In one embodiment, distal portion 1042 and tip 1014c of dissecting tip 1014 have substantially round cross-sections which may be substantially circular, oblong or oval. The diameter of the cross-sections may decrease from the proximal end of distal portion 1042 towards distal tip 1014c. In one embodiment, the diameter of distal tip 1014c is from about 2 mm to about 4 mm. In another embodiment, distal tip 1014c has a diameter of from about 4 mm to about 6 mm. It is also contemplated that proximal portion 1040 may also have a round cross-section which may decrease in diameter along its length. Providing a bulbous larger diameter distal tip and a reduced diameter or width proximal of a distal tip will increase visibility at the tip to the surgeon.

Curved inner and/or outer surfaces 1014a and 1014b, respectively may be formed having any suitable radius of curvature which may define an arc of between about 5.degree. to about 90.degree. In one embodiment the arc defined by curved inner and outer surfaces 1014a and 1014b is between about 50.degree. and 90.degree. In another embodiment the arc is between about 60.degree. and about 80.degree. and in another embodiment (FIG. 16) the arc is between about 80.degree. and about 90.degree. It is also contemplated that curved inner and/or outer surfaces 1014a and 1014b may be formed having a plurality of different radii of curvature.

The distance "X" (FIG. 16a) between a horizontal plane "Y" defined by tissue contacting surface 1034a of anvil assembly 1034 and distal tip 1014c may be between about 10 mm and about 30 mm. In one embodiment, the distance X is between about 25 mm and about 30 mm. It is noted that distance X may vary greatly depending on the type of instrument dissecting tip 1014 is employed on, e.g., open or endoscopic, and on the particular procedure the instrument is being employed to perform. Accordingly, a wide size range of dissecting tips is envisioned.

Figure 17A:
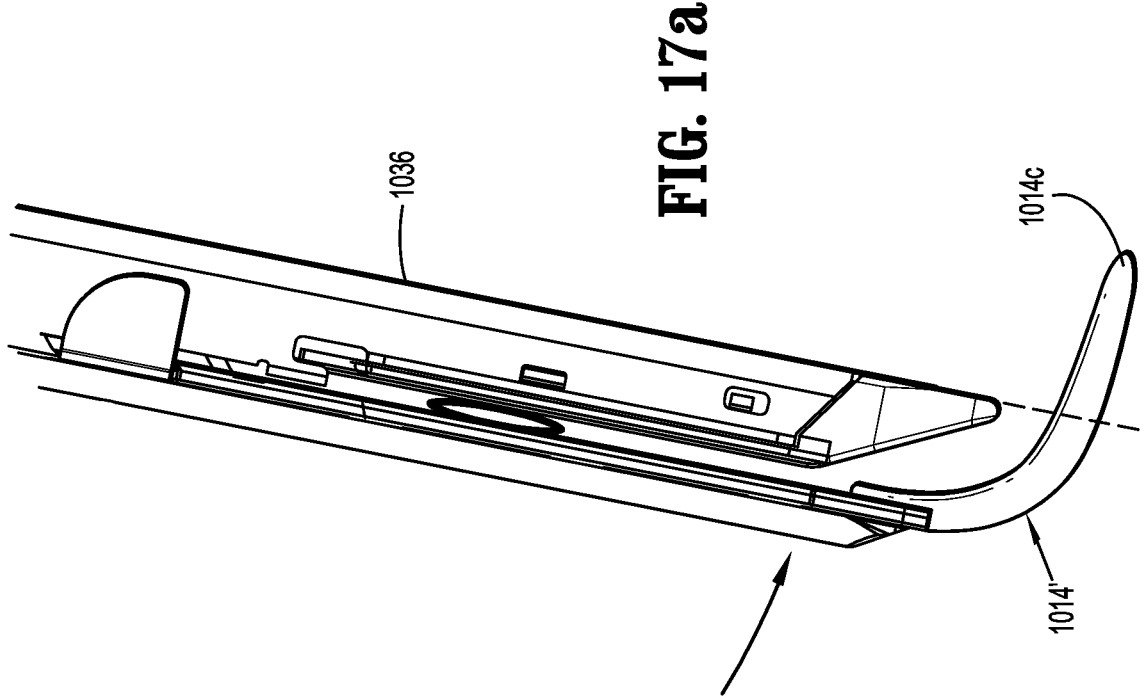
FIG. 17a is a side view of the end effector and dissecting tip shown in FIG. 17 with the anvil assembly and cartridge assembly of the end effector in the clamped position.
Figure 17:
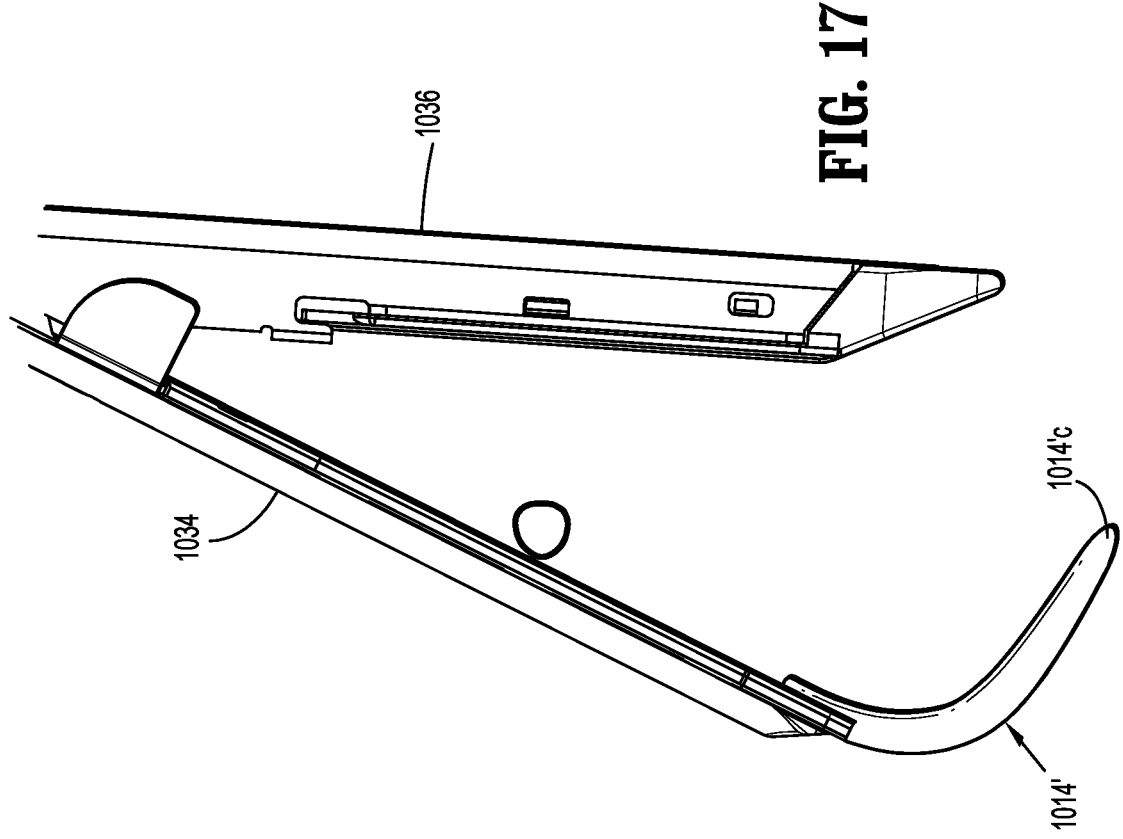
FIG. 17 is a side view of another embodiment of the presently disclosed dissecting tip attached to an end effector of a surgical instrument with the anvil assembly and the cartridge assembly of the end effector in an open position.

In one embodiment (FIGS. 17 and 17a), distal portion 1042' including distal tip 1014c extends below a plane "Z" defined by the bottom surface of cartridge assembly 1036. By extending distal portion 1042' of dissecting tip 1014' below the plane defined by cartridge assembly 1036, access to adherent tissue may be improved and improved visualization of dissecting tip 1014' is provided. Visualization of dissecting tip 1014' facilitates confirmation that the dissecting tip is properly positioned and that dissection of adherent tissue is completed. This embodiment may be more suitable for use on instruments designed for open surgical procedures since an enlarged enlargeable trocar would be required to facilitate passage of dissecting tip 1014'.

It will be understood that various modifications may be made to the embodiments disclosed herein. For example, the dissecting tip may be secured to other parts of the end effector including the cartridge assembly. Further, each of the dissecting tips may be monolithically or integrally formed with or removably attachable to the end effector, e.g., anvil assembly or cartridge assembly. Moreover, the angles and/or curves of the dissecting tip surface(s) may be modified to better suit, e.g., provide better access to difficult to reach tissue in a particular surgical procedure. It is also envisioned that any of the dissecting tips described above may be incorporated into other surgical instruments which may require some tissue dissection or manipulation prior to use. These instruments include surgical clip appliers and other ligation devices. Further, it is understood that within reason what has been stated as contemplated or envisioned, as applicable for one embodiment is applicable to the other embodiments disclosed or contemplated herein. Therefore, the above description should not be construed as limiting, but merely as exemplifications of preferred embodiments. Those skilled in the art will envision other modifications within the scope and spirit of the claims appended hereto.

What is claimed is:

1. A surgical stapling assembly, comprising:
   an anvil assembly having a tissue contacting surface and a plurality of staple forming pockets;
   a cartridge assembly having a plurality of surgical staples arranged in rows, the anvil assembly and cartridge assembly being pivotally movable in relation to each other between an open position and a closed position; and
   a dissecting tip extending from the anvil assembly and having a rounded blunt tip and smooth surfaces, the dissecting tip having an inner surface that is contiguous with the tissue contacting surface of the anvil assembly, the inner surface of the dissecting tip extending downwardly toward the cartridge assembly, the width of the dissecting tip decreasing from a proximal end to a distal end, the dissecting tip being integrally formed with the anvil assembly and spaced from the cartridge assembly when the cartridge assembly and anvil assembly are in the closed position.

2. The surgical tool assembly according to claim 1, wherein the anvil assembly and cartridge assembly form an end effector that articulates with respect to an endoscopic portion.

3. The surgical tool assembly according to claim 1, wherein the cartridge assembly has a plurality of staple slots for receiving the surgical staples.

4. The surgical tool assembly according to claim 3, further comprising a knife that translates distally through the cartridge assembly and wherein the cartridge assembly defines a slot for the passage of the knife.

5. The surgical tool assembly according to claim 1, further comprising a handle assembly.

6. The surgical tool assembly according to claim 1, wherein the anvil assembly and cartridge assembly are attached to an endoscopic portion.

7. The surgical tool assembly according to claim 1, wherein the anvil assembly and cartridge assembly are attached to a proximal body portion that attaches to a handle assembly.

8. The surgical tool assembly according to claim 1, wherein the anvil assembly and cartridge assembly form an end effector that is adapted to access a surgical site through a trocar cannula assembly.

9. The surgical tool assembly according to claim 1, wherein the dissecting tip does not extend below a plane defined by a bottom surface of the cartridge assembly.

10. The surgical tool assembly according to claim 1, wherein the anvil assembly and dissecting tip are formed from a surgical grade metal.

11. A surgical stapling assembly, comprising:
    an anvil assembly having a tissue contacting surface and a plurality of staple forming pockets;
    a cartridge assembly having a plurality of surgical staples arranged in rows, the anvil assembly and cartridge assembly being pivotally movable in relation to each other between an open position and a closed position; and
    a dissecting tip extending from the anvil assembly and having a proximal end, a distal end, a rounded blunt tip, and smooth surfaces, the dissecting tip having an inner surface that is contiguous with the tissue contacting surface of the anvil assembly and spaced from the cartridge assembly when the cartridge assembly and anvil assembly are in the closed position, the inner surface of the dissecting tip extending downwardly toward the cartridge assembly, the width of the dissecting tip decreasing from the proximal end to the distal end, the dissecting tip being integrally formed with the anvil assembly.

12. The surgical tool assembly according to claim 11, further including an endoscopic portion, wherein the anvil assembly and cartridge assembly form an end effector, the end effector that articulating with respect to the endoscopic portion.

13. The surgical tool assembly according to claim 11, wherein the cartridge assembly has a plurality of staple slots for receiving the surgical staples.

14. The surgical tool assembly according to claim 13, further comprising a knife that translates distally through the cartridge assembly, wherein the cartridge assembly defines a slot for the passage of the knife.

15. The surgical tool assembly according to claim 11, further comprising a handle assembly.

16. The surgical tool assembly according to claim 15, further including an endoscopic portion extending from the handle assembly, wherein the anvil assembly and cartridge assembly are attached to the endoscopic portion.

17. The surgical tool assembly according to claim 15, further including a proximal body portion, wherein the anvil assembly and cartridge assembly are attached to the proximal body portion and the proximal body portion is attached to the handle assembly.

18. The surgical tool assembly according to claim 11, wherein the anvil assembly and cartridge assembly form an end effector that is adapted to access a surgical site through a trocar cannula assembly.

19. The surgical tool assembly according to claim 11, wherein the dissecting tip does not extend below a plane defined by a bottom surface of the cartridge assembly.

20. The surgical tool assembly according to claim 11, wherein the anvil assembly and dissecting tip are formed from a surgical grade metal.

* * * * *